(12) United States Patent
Fox

(10) Patent No.: US 8,721,646 B2
(45) Date of Patent: May 13, 2014

(54) METHODS AND APPARATUS FOR A STAPLE

(76) Inventor: William Casey Fox, Pipe Creek, TX (US)

( * ) Notice: Subject to any disclaimer, the term of this patent is extended or adjusted under 35 U.S.C. 154(b) by 563 days.

(21) Appl. No.: 11/545,273

(22) Filed: Oct. 10, 2006

(65) Prior Publication Data

US 2008/0161808 A1 Jul. 3, 2008

(51) Int. Cl.
*A61F 2/30* (2006.01)

(52) U.S. Cl.
USPC .......................................................... 606/75

(58) Field of Classification Search
USPC ............ 606/60, 75, 139, 142, 143, 151, 155, 606/219, 220, 221, 227, 300–331
See application file for complete search history.

(56) References Cited

U.S. PATENT DOCUMENTS

| | | | |
|---|---|---|---|
| 3,174,851 A | 3/1965 | Buehler et al. | 75/170 |
| 4,047,524 A | 9/1977 | Hall | 128/69 |
| 4,170,990 A | 10/1979 | Baumgart et al. | 128/92 B |
| 4,263,903 A | 4/1981 | Griggs | 128/92 B |
| 4,278,091 A | 7/1981 | Borzone | 128/334 |
| 4,321,002 A | 3/1982 | Froehlich | 411/457 |
| 4,434,796 A | 3/1984 | Karapetian et al. | 128/335 |
| 4,454,875 A | 6/1984 | Pratt et al. | 128/92 |
| 4,570,623 A | 2/1986 | Ellison et al. | 128/92 |
| 4,665,906 A | 5/1987 | Jervis | 128/92 |
| 4,723,540 A | 2/1988 | Gilmer, Jr. | 128/92 |
| 4,756,711 A | 7/1988 | Mai et al. | 623/23 |
| 5,002,563 A | 3/1991 | Pyka et al. | 606/222 |
| 5,046,513 A | 9/1991 | Gatturna et al. | 128/898 |
| 5,053,038 A | 10/1991 | Sheehan | 606/75 |
| 5,067,957 A | 11/1991 | Jervis | 606/108 |
| 5,089,009 A | 2/1992 | Green | 606/219 |
| 5,108,395 A | 4/1992 | Laurain | 606/61 |
| 5,209,756 A | 5/1993 | Seedhom et al. | 606/151 |
| 5,222,975 A | 6/1993 | Crainich | 606/219 |
| 5,304,204 A | 4/1994 | Bregen | 606/219 |
| 5,324,307 A | 6/1994 | Jarrett et al. | 606/219 |
| 5,342,396 A | 8/1994 | Cook | 606/219 |
| 5,352,229 A | 10/1994 | Goble et al. | 606/72 |

(Continued)

OTHER PUBLICATIONS

Beynet, Patrick, "Production of a Fracture-Reducing Staple Using Ti-Ni Shape Memory Alloys," University of Poincare (Nancy1), France, 1994.

(Continued)

*Primary Examiner* — Kevin T Truong
*Assistant Examiner* — Christopher Beccia
(74) *Attorney, Agent, or Firm* — Greenberg Traurig, LLP; Ross Spencer Garsson

(57) ABSTRACT

A staple constructed from shape memory material provides the ability to move from a first shape to any point up to and including a second shape. The staple includes a bridge having a first member and a second member, and allows the second member of the bridge to change elevation with respect to the first member, thereby creating compressive forces, offset forces, or distraction forces. Upon the application of energy, the second member moves upward or downward to deliver forces, dependent upon a desired effect. The staple further includes first and second legs for attaching to first and second bones. The offsetting forces may be utilized to offset the second bone relative to the first bone, or to align offset bones. The bridge may include a transition member or plurality of transition members in communication with the first and second members, whereby the transition member moves about the first member.

5 Claims, 21 Drawing Sheets

(56) References Cited

U.S. PATENT DOCUMENTS

| | | | |
|---|---|---|---|
| 5,366,479 A * | 11/1994 | McGarry et al. | 606/219 |
| 5,395,372 A | 3/1995 | Holt et al. | 606/61 |
| 5,449,359 A | 9/1995 | Groiso | 606/75 |
| 5,454,814 A | 10/1995 | Comte | 606/75 |
| 5,551,871 A | 9/1996 | Besselink et al. | 433/5 |
| 5,597,378 A | 1/1997 | Jervis | 606/78 |
| D378,409 S | 3/1997 | Michelson | D24/145 |
| 5,645,599 A | 7/1997 | Samani | 623/17 |
| 5,660,188 A | 8/1997 | Groiso | 128/898 |
| 5,728,127 A | 3/1998 | Asher et al. | 606/61 |
| 5,785,713 A | 7/1998 | Jobe | 606/69 |
| 5,788,698 A * | 8/1998 | Savornin | 606/75 |
| 5,853,414 A | 12/1998 | Groiso | 606/75 |
| 5,876,434 A | 3/1999 | Flomenblit | 623/1 |
| 5,941,890 A | 8/1999 | Voegele et al. | 606/151 |
| 6,083,242 A | 7/2000 | Cook | 606/219 |
| 6,325,805 B1 | 12/2001 | Ogilvie et al. | 606/75 |
| 6,440,135 B2 | 8/2002 | Orbay et al. | 606/69 |
| 6,723,131 B2 | 4/2004 | Muschler | 623/23.51 |
| 6,736,799 B1 | 5/2004 | Erbe et al. | 604/181 |
| 6,966,911 B2 * | 11/2005 | Groiso | 606/75 |
| 7,056,330 B2 * | 6/2006 | Gayton | 606/219 |
| 2002/0019636 A1 * | 2/2002 | Ogilvie et al. | 606/75 |
| 2002/0029044 A1 * | 3/2002 | Monassevitch et al. | 606/75 |
| 2004/0002710 A1 * | 1/2004 | Han et al. | 606/72 |
| 2007/0239278 A1 * | 10/2007 | Heinz | 623/17.15 |

OTHER PUBLICATIONS

Beynet, Patrick, "Bibliography of Shape Memory Alloys," 1993-1994, Laboratory of Science and Engineering of Surfaces, University of Poincare (Nancy1), France.

Knox, Glenn W. and Reitan, Harlan, "Shape-Memory Stapes Prosthesis for Otosclerosis," Laryngscope 115, Aug. 2005.

Ryhanen, J., et al., "Bone healing and Mineralization, Implant Corrosion, and Trace Metals after Nickel-Titanium Shape Memory Metal Intramedullary Fixation," John Wiley and Sons, Inc., J Biomed Res, 47, 472-482, 1999.

Memometal Technologies brochure, Memoclip Shape Memory Staples, Campus de Ker Lann, Rue Blaise Pascal, 351790 BRUZ—France.

Memodyn brochure, Memodyn Compression Staples, Manufacturer: BRI—Les Mas des 3 Dauphins, 83340 Le Luc (France), Distributor: Austin and Associates, Inc., TELOS Medical.

Orthomed brochure, Agrafes Orthomed, Cote de Azur—France.

Orthomed brochure, Agrafes Ligamentaires, Cote de Azur—France.

A.M.F. brochure, L'agrafe d'osteosynthese, Route de Quincy, 18120 Lury sur Arnon, France.

Tremblay, Melisa, 37 Les implants medicaux en alliage a memoire de forme.

Medinov AMP brochure, "Agrafe a memoire de forme," 24 rue Francis de Pressense—BP 2175.

* cited by examiner

METHODS AND APPARATUS FOR A STAPLE

BACKGROUND OF THE INVENTION

1. Field of the Invention

The present invention relates to shape memory materials, and, more particularly, but not by way of limitation, to methods and an apparatus for utilizing a shape memory staple as an aid in operations including osteologic synthesis.

2. Description of the Related Art

Wire and staple fixation of bone have been used clinically for over 50 years. Cerclage techniques have commonly been used to encircle bone with wire to secure it to an adjacent bony segment. Variants of this technique initially involved taking a cerclage wire and bending it into a U-shape and inserting it into bone to provide intrabony fixation. As time progressed specialized staple with two of four legs were developed. These staple implants were fabricated from materials such as stainless steel and chromium-cobalt alloys and impacted into bone or placed so that the legs of the staple were inserted in drill holes thus minimizing surgery induced fracture at the implant site. As the use of staples expanded they were often contoured so as to match the anatomy of the site. Several examples of contoured staples exist such as the Richard's Krackow HTO, Krackow HTO Blage Staple, and Osteotomy Fixation Staple all from Smith & Nephew, Inc.; Semi-oblique and Offset Staple from Orthomed, S.A. and Tibial Osteotomy Staple, Memometal, Industries. These implants have been designed to contour to the bone surfaces where they are placed.

In the last 20 years, nickel-titanium staples have been used for their shape changing properties. These staples can be designed to retract their U-shaped legs so as to bring bone segments together. Like their predecessors they have also been contoured to match the anatomy of bone as illustrated by the Tibial Osteotomy Staple of Memometal Industries. This specific design uses a step in height to contour to the tapering portion of the tibia near the knee. This bony contour steps down from the width of the knee to the width of the shaft and can be well accommodated by the step staple. Though this staple has legs that deflect inwards during heating its stepped back does not change shape due to the undesired consequence of this shape change causing lifting of the back of the staple from the surface of the bone. This lifting would, in the application of the high tibial osteotomy, reduce the quality of fixation because the legs would partially pull out of bone and the back of the staple would be prominent and visible under the skin. These concerns have limited the applications of step staples to adapting to anatomical contours and taught against implants that change the shape of their back in all planes except the plane of the surface of the bone.

Accordingly the subject of this invention, a shape memory staple that provides restraint forces in multiple planes would be beneficial to surgeons, as well as persons requiring bone surgeries, because the shape changing back of the staple would not lift from bone such as in the high tibial osteotomy example but will compress the bone together while displacing them relative to one another.

SUMMARY OF THE INVENTION

In accordance with the present invention, a staple constructed from shape memory material compresses two bone segments together while applying offsetting forces provides a surgeon a unique new tool in the treatment of the human skeleton. In particular, the staple changes shape out of the plane of the bone surface, thereby causing the bone to be shifted versus the staple being lifted. By way of example, a surgeon may displace a joint so as to create a new alignment to straighten a deformity. In another example, a surgeon may move a joint of the spine back into alignment following two vertebra slipping relative to one another. Here compression and simultaneous offset forces are exerted so as to realign bones, correct a deformity, or realign slipped vertebra.

The staple according to the invention includes a first shape and a second shape, and a bridge having a first member and a second member, wherein the second member moves relative to the first member, thereby delivering a vertical displacement and an offset force. In a first embodiment, the second member moves downward and towards the first member to deliver a combination of offsetting and contraction forces across the bridge. The staple further includes legs disposed on the bridge, such that the legs secure the staple to first and second bones that require an offset. Upon the transformation from the second shape to the first shape, the staple forces the second bone to move downward with respect to the first bone, and restrains the bones in the offset position.

In a second embodiment, the second member moves upward to extend a bridge width, thereby delivering a distraction force across the bridge and any legs disposed on the bridge. The upward movement further creates an offset force that may be utilized to reposition bones to anatomically correct positions relative to each other. Accordingly, it is possible to distract a first bone from a second bone, and reposition bones that have been dislodged bones.

It is therefore an object of the present invention to change shape to provide compression through a staple with a back section having two levels that change position relative to one another so as to decrease or increase the distance between the legs of the staple and simultaneously offset the two bone fragments or bring the two bone fragments into alignment.

It is a further object of the present invention to fabricate the implant of shape changing materials that are biocompatible.

It is still further an object of the present invention to provide a method to offset bone segments or realign bone segments that have become offset.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

DETAILED DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

Figure 1A:
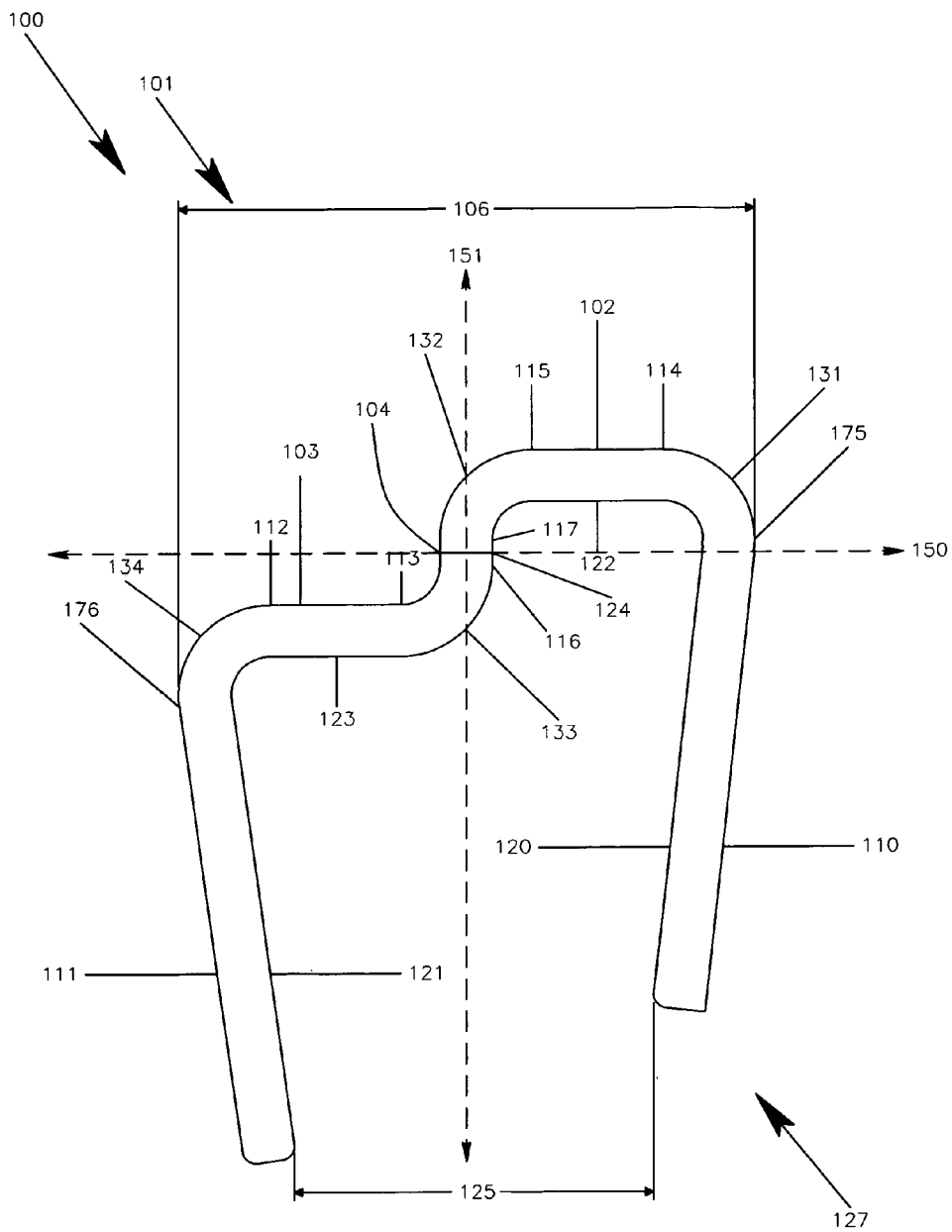
FIG. 1A provides a frontal view of a staple according to a first embodiment.
Figure 1B:
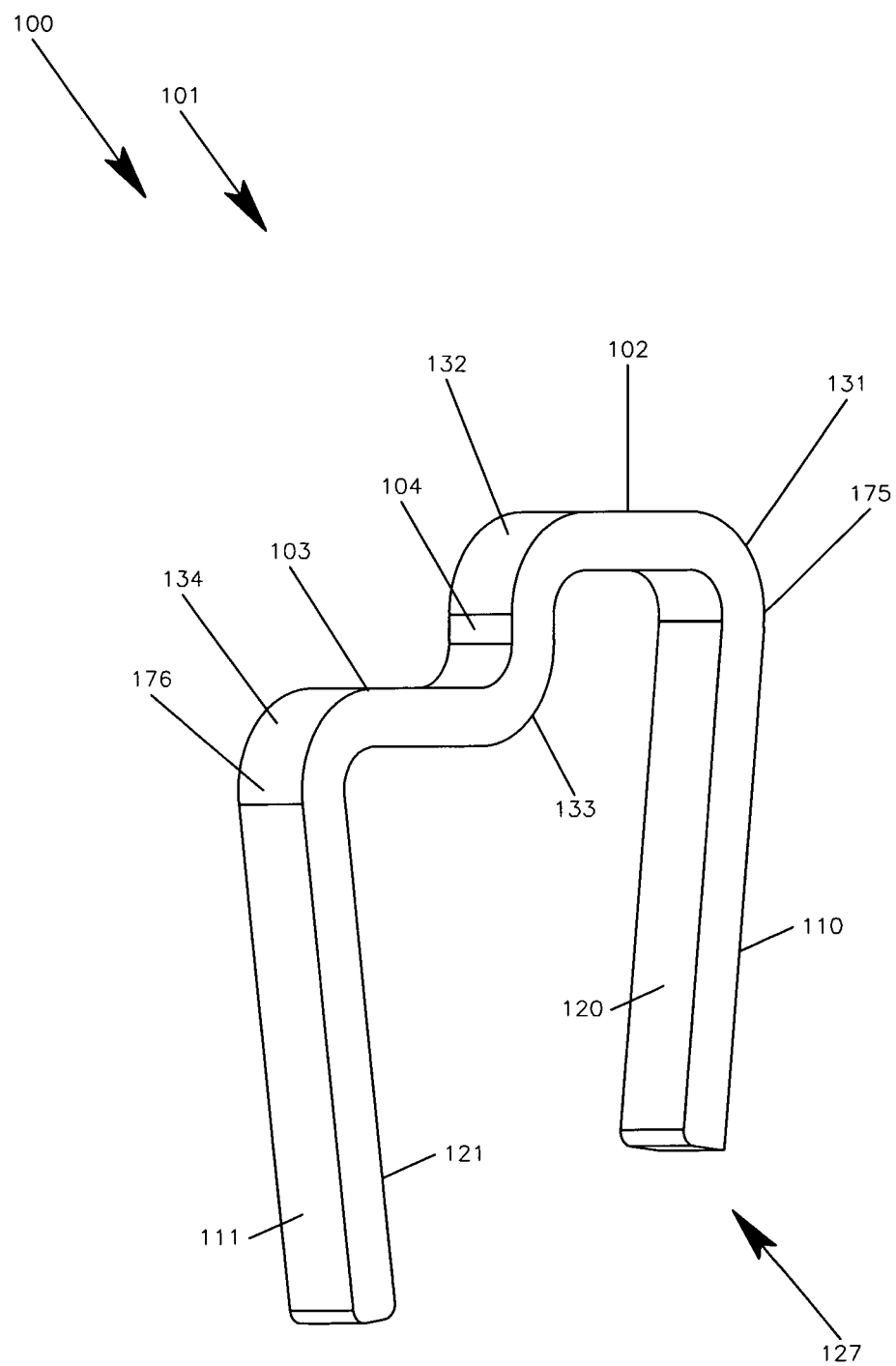
FIG. 1B provides a perspective view of the staple according to the first embodiment.
Figure 1C:
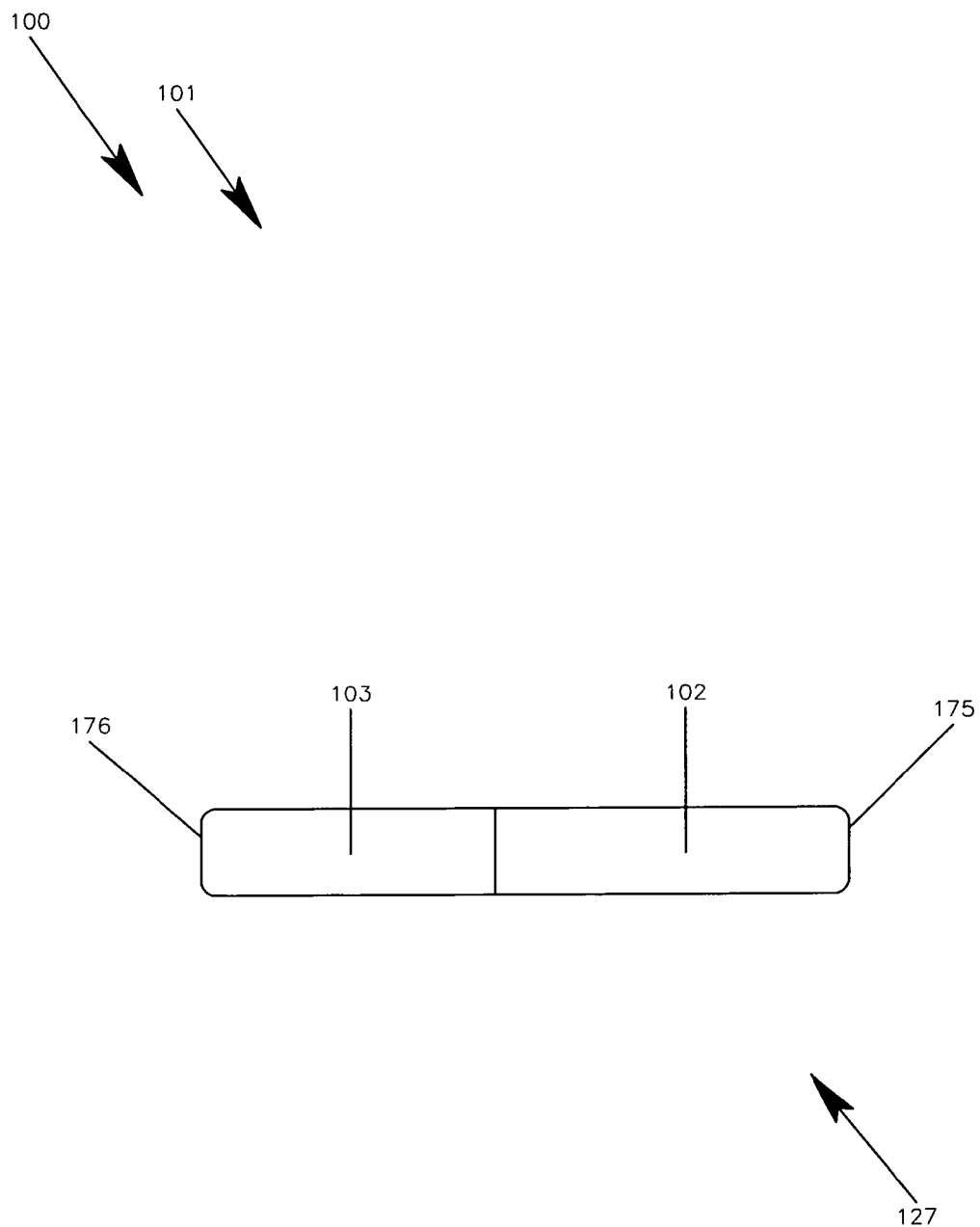
FIG. 1C provides a top view of the staple according to the first embodiment.
Figure 1D:
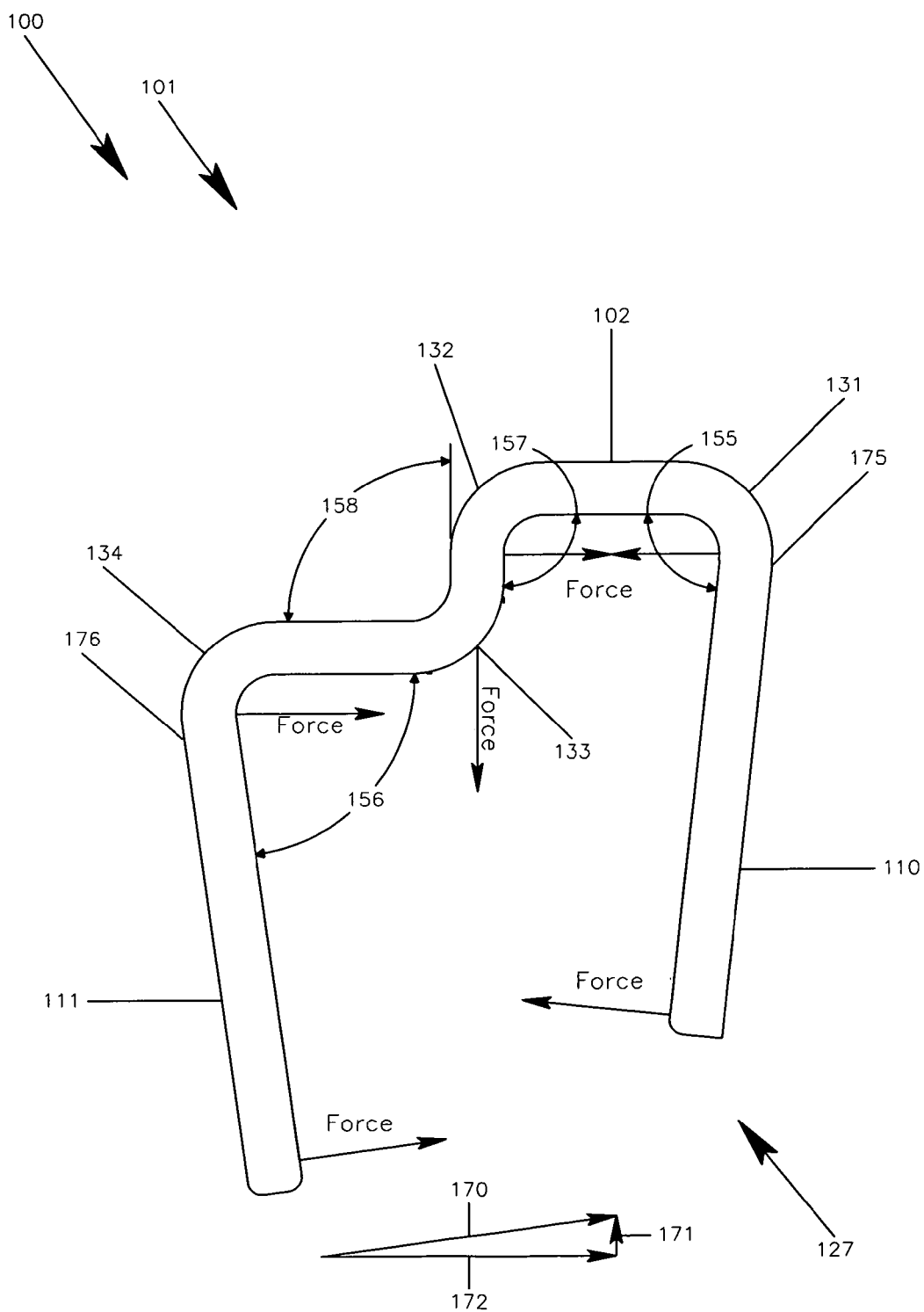
FIG. 1D provides frontal view illustrating some of the forces generated by the staple according to the first embodiment.
Figure 2A:
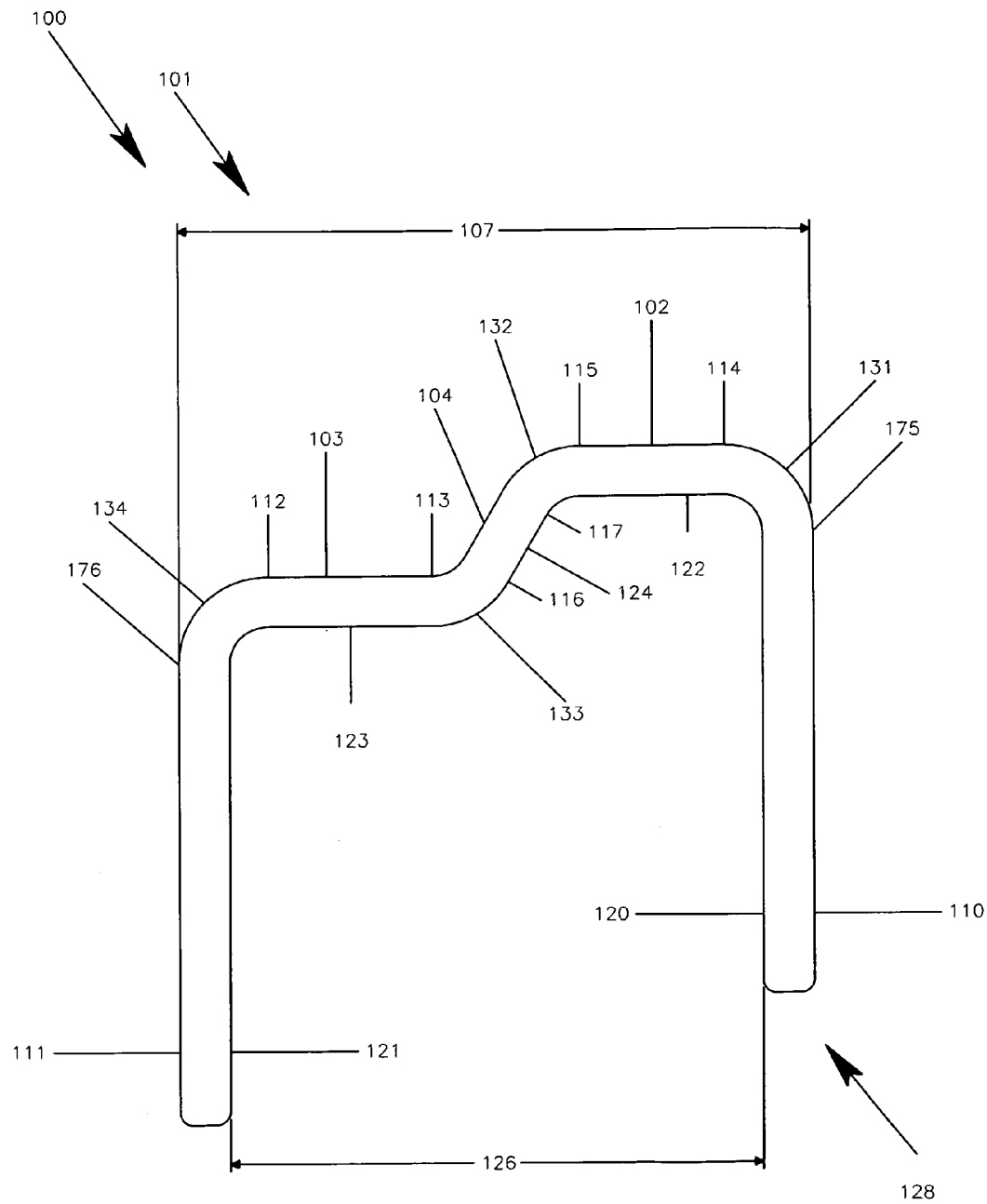
FIG. 2A provides a frontal view of the staple in a second position according to the first embodiment.
Figure 2B:
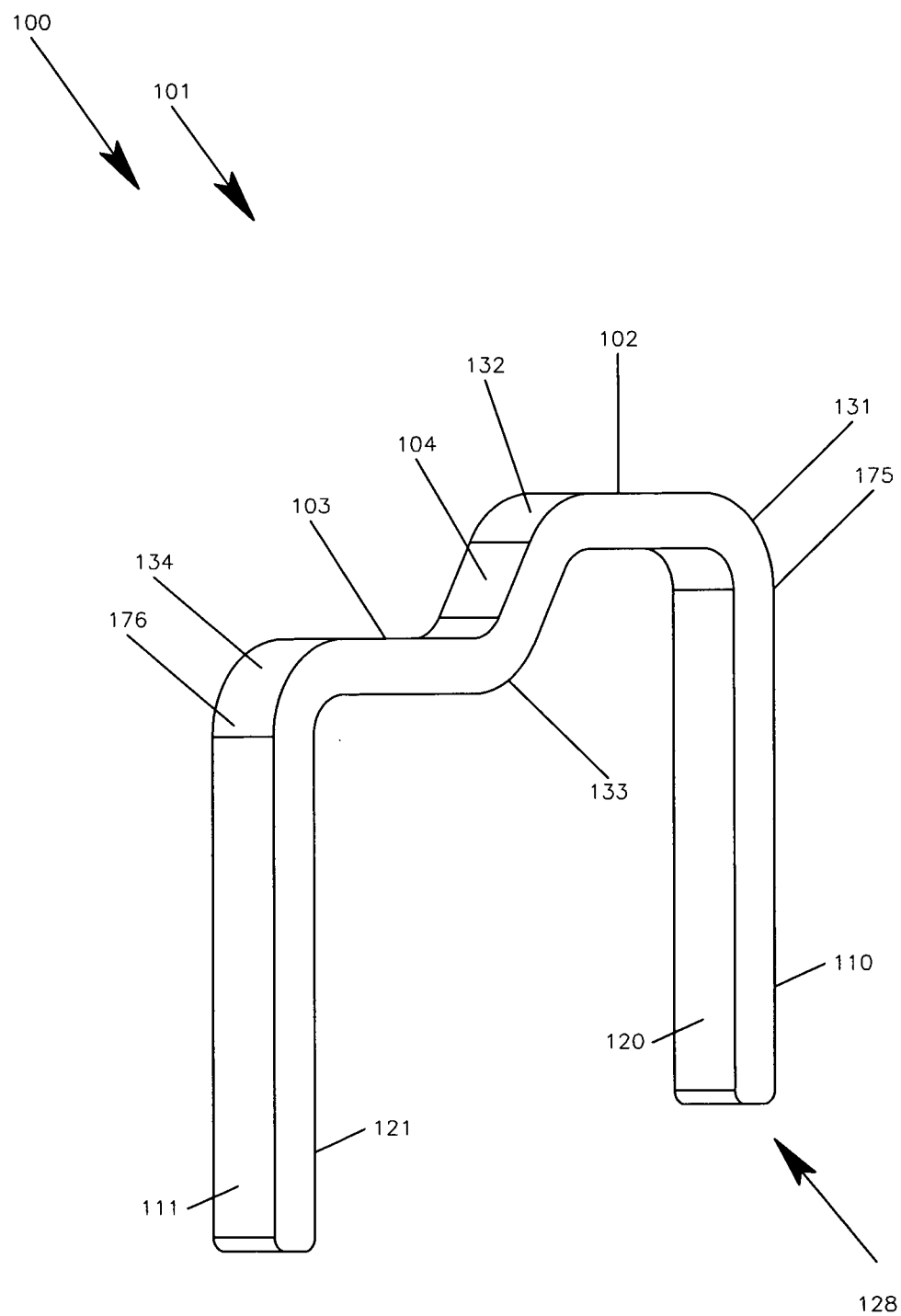
FIG. 2B provides a perspective view of the staple according to the first embodiment.
Figure 2C:
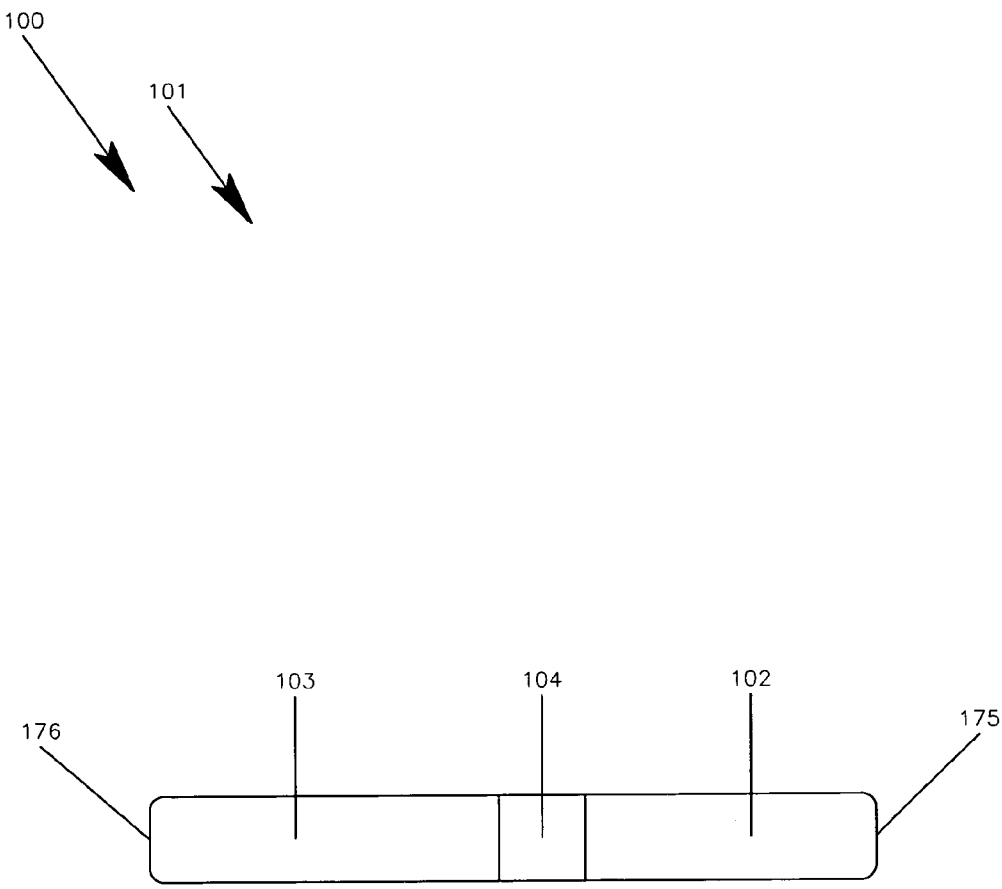
FIG. 2C provides a top view of the staple in the second position according to the first embodiment.
Figure 2D:
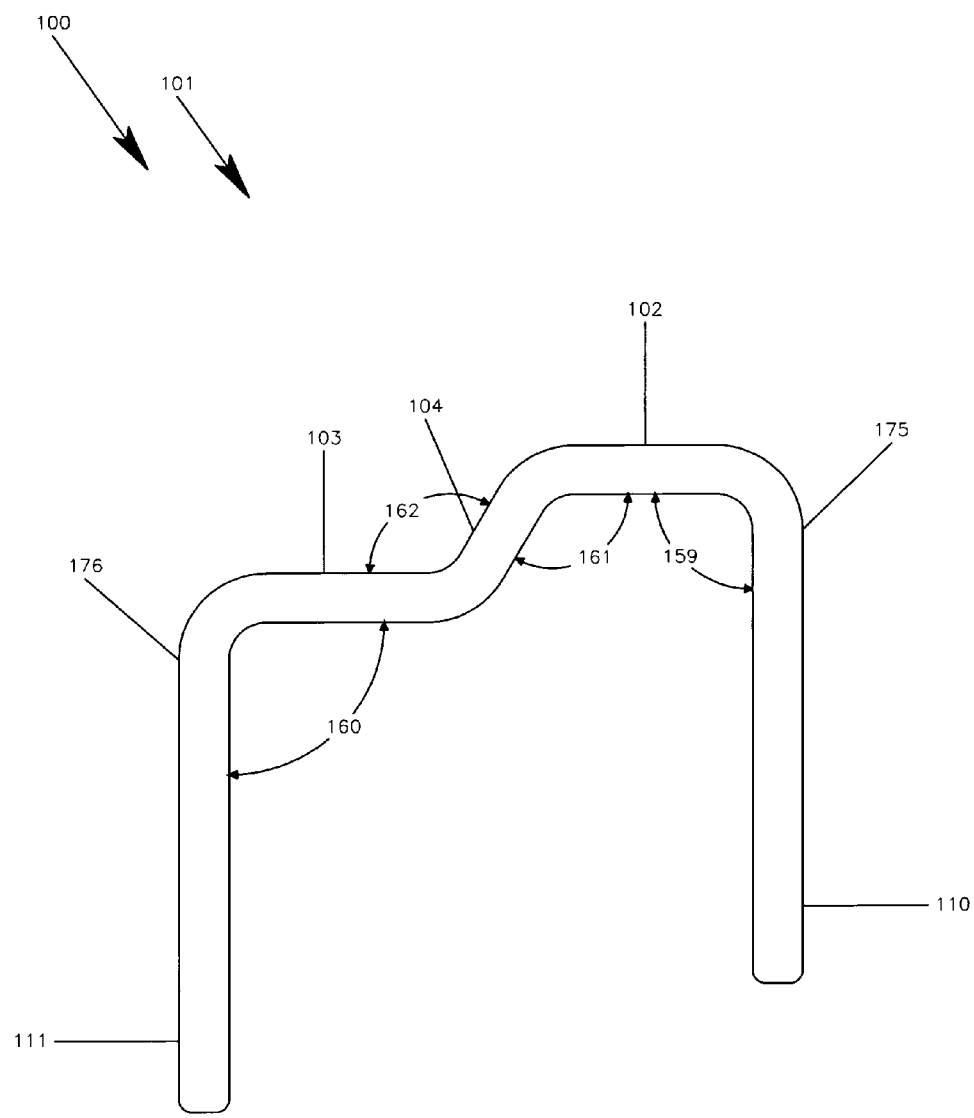
FIG. 2D provides a frontal view of the staple, and further showing angle associated with the second position of the first embodiment.

As illustrated in FIGS. 1A-2C, a staple 100 may be constructed from virtually any alloy exhibiting a shape-memory effect. Examples of shape memory effect materials include, but are not limited to nitinol, AuCd, $FePt_3$, beta Brass, and InTI. Shape memory effect materials allow an object to be: formed in an original shape; deformed while in a martensitic state; heated to a point where the deformed object phase changes from the martensitic state to an austenitic state, thereby returning the deformed object to its original shape; and cooled such that the object retains the original shape. Accordingly, the staple 100 is formed in an original or first shape 127 (FIGS. 1A-1C), and annealed to set its original shape. The staple 100, while cold and in its martensitic phase, is then deformed to a second shape 128 (FIG. 2A-2C). Next, the staple 100 is heated until it phase changes to an austenitic phase, thereby returning from the deformed or second shape 128 to the original or first shape 127. Finally, the staple 100 cools whereby the staple 100 retains the original first shape 127.

While this embodiment has been shown with the staple 100 moving from the second shape to the first shape, it should be apparent that the staple 100 is usable at virtually any point along the transition between the second shape and the first shape. Accordingly, an end-use shape may designate any shape between the second shape 128 and up to and including the first shape 127. The amount of heat energy applied to the deformed shape determines the amount of transition from the second shape 128 to the first shape 127.

The staple 100 includes a first leg 110, a second leg, 111, and a bridge 101, which, in the first shape 127, has a bridge width 106, and in the second shape 128, has a bridge width 107. The bridge 101 has a first end 175 and a second end 176 and includes a first member 102, a second member 103, and a transition member 104. In this example, the first member 102 and the second member 103 are planar, however, one of ordinary skill in the art will recognize that the shape of the member 102 and 103 may be of any form, including, arcs, angles, and the like. In this embodiment, the first leg 110 is connected to a first end 114 of the first member 102, and a second end 115 of the first member 102 is connected to a first end 117 of the transition member 104. The second leg 111 is connected to a first end 112 of the second member 103, and a second end 113 of the second member 103 is connected to a second end 116 of the transition member 104. The staple 100 further includes a first bend 131 disposed between the first leg 110 and the first member 102, a second bend 132 disposed between the first member 102 and the transition member 104, a third bend 133 disposed between the transition member 104 and the second member 103, and a fourth bend 134 disposed between the second member 103 and the second leg 111.

For the purpose of clarity and to provide reference points, a horizontal axis 150 and a vertical axis 151 have been provided. One of ordinary skill in the art will recognize that references to horizontal and vertical directions are complementary to the cited axes 150 and 151. It should further be understood that a vertical plane is defined as a plane passing through the vertical axis 151 and the horizontal axis 150, and a horizontal plane is perpendicular to the vertical plane. Additionally, the term "elevation" is utilized in reference to vertical displacement, wherein a lower elevation is recognized below the horizontal axis 150 and a higher elevation is recognized above the horizontal axis 150. As such, an object may move from a given elevation to a higher or lower elevation.

The staple 100 further includes a first engagement surface 120, a second engagement surface 121, a third engagement surface 122, a fourth engagement surface 123, and a fifth engagement surface 124. The engagement surfaces 120 through 123 may extend along the complete length of the staple 100 dependent upon the cross-section of the staple 100. In this first embodiment, the first engagement surface 120 is disposed on an inner portion of the first leg 110, and the second engagement surface 121 is disposed on an inner portion of the second leg 111. The third engagement surface 122 is disposed on an inner portion of the first member 102, the fourth engagement surface 123 is disposed beneath the second member 103, and the fifth engagement surface 124 is disposed on an inner portion of the transition member 104. In this first embodiment, the staple 100 includes a rectangular cross-section; however, one of ordinary skill in the art will recognize that other cross-section shapes are possible, including square, round, oblong, or portions thereof.

In the first shape 127, as shown in FIGS. 1A-1C, the first member 102 is disposed substantially parallel to the horizontal axis 150. The second member 103 is disposed offset and substantially parallel to the first member 102, and the first leg 110 and the second leg 111 are disposed substantially at equal angles to the respective connecting members 102 and 103. The first leg 110 is disposed at an angle 155 relative to the first member 102, and the second leg 111 is disposed at an angle 156 relative to the second member 103. Illustratively, the first and second legs 110 and 111 are disposed approximately sixty degrees from the first and second members 102 and 103. However, one of ordinary skill in the art will recognize that other angles may be utilized, dependent upon a desired retention force. The first and second legs 110 and 111 extend in the same direction from the bridge 101, such that the first leg 110 and the second leg 111 are angled toward each other, and have an internal clearance 125. The transition member 104 is disposed at an angle 157 relative to the first member 102, and at an angle 158 relative to the second member 103. In this example of the first shape 127, the transition member 104 is disposed substantially perpendicular from the planes of the first member 102 and the second member 103. It should be understood that the relationships among the first and second members 102 and 103, the first and second legs 110 and 111, and the transition member 104, as described above are exemplary only, and that these relationships may be selected dependent upon a desired bone compression force or bone offset. Illustratively, the first member 102 and the second member 103 could lie in intersecting planes, the angles of the legs 110 and 111 may be different, and the transition member 104 does not have to be disposed perpendicular to the members. Additionally, the lengths of the first and second members 102 and 103, or the lengths of the transition member 104 may be adjusted to deliver varying results, and, accordingly, all such adjustments should be construed as part of this disclosure.

In the second shape 128, the staple 100 is deformed as shown in FIGS. 2A-2D, such that the first member 102 and the second member 103 are offset and substantially parallel to each other, and the first leg 110 and the second leg 111 are substantially perpendicular to the first member 102 and the second member 103. As such, the first bend 131 is extended to an angle 159, and the fourth bend 134 is extended to an angle 160. Illustratively, the angles 159 and 160 span approximately ninety degrees. Similarly, the second bend 132 extends to angle 161, and the third bend 133 extends to angle 162, such that the transition member 104 is disposed at an angle relative to the first member 102 and the second member 103, thereby increasing the clearance between the legs 110 and 111 to an internal clearance 126. Illustratively, the transition member 104 is disposed at an angle of approximately sixty degrees relative to the first and second members 102 and 103. While this staple 100 has been shown with the legs 110 and 111 substantially perpendicular to the first and second members 102 and 103, and the transition member 104 disposed at an angle of approximately sixty degrees relative to the first and second members 102 and 103, one of ordinary skill in the art will recognize that other angles besides those shown may be utilized to deliver varying forces and lateral displacements. It should further be recognized that the use of parallel legs is conducive to insertion of a staple into pre-drilled holes, however, other angles may be utilized to address alternative situations, including the insertion of one leg at a time.

Upon the application of heat energy from the temperature of the body or sources including but not limited to resistive, conductive or inductive heating, the staple 100 in a deformed or second shape 128 (deformed martensitic phase), commences to change from the martensitic state to the austenitic state. While application of heat energy is preferred, those of ordinary skill in the art will recognize that application in any form that results in shape change of the staple 100 may be used. Upon completion of the austenitic phase change, the staple 100 has returned to the original or first shape 127. Upon cooling, the staple 100 retains the original or first shape 127. One of ordinary skill in the art will recognize that upon the transformation of a shape memory alloy to the original shape 127, a force is created, and accordingly, the staple 100 may be utilized in applications where retaining and residual forces are required. The resulting shape change causes forces for bone compression and for holding the desired bone offset.

In this first embodiment, the phase change from the deformed or second shape 128 to the original or first shape 127 creates forces as shown in FIG. 1D. The first bend 131 moves in an arc from the angle 159 (approximately ninety degrees) to a second more acute angle 155 (approximately sixty degrees), thereby rotating the first leg 110 a prescribed distance toward the second leg 111. In a similar fashion, the fourth bend 134 moves from the angle 160 that is substantially perpendicular relative to the second member 103 to the angle 156 that is a more acute angle, thereby rotating the second leg 111 towards the first leg 110 a prescribed distance. Illustratively, in this first embodiment, the first leg 110 rotates inward such that an end of the second leg 111 is potentially any position between its first and second shape 127 and 128, but for this example, approximately two millimeters from its position in the second shape 128.

Additionally, the second bend 132 moves from the angle 161 (obtuse) to angle 157 (substantially perpendicular), and the third bend 133 moves from the angle 162 (obtuse angle position associated with the second shape 128) to the angle 158 (substantially perpendicular angle associated with the first shape 127). Accordingly, in the first shape 127 the transition member 104 is in a position that is substantially perpendicular relative to the first member 102 and the second member 103. The rotation of the transition member 104 to the perpendicular position of the first shape 127 pulls the second member 103, the fourth bend 134, and the second leg 111 toward the first leg 110, such that the bridge width 106 of the first shape 127 is less than the bridge width 107 of the second shape 128, thereby providing a translation component having increased compressive forces and an offset component. As such, the end of the second leg 111 experiences an increased displacement over the end of the first leg 110. The translation component of this invention is predominantly utilized to draw bone segments together for increased localized fusion, and to force one bone into an offset position relative to a second bone.

In this first embodiment, compressive forces are created between the first engagement surface 120 and the second engagement surface 121, thereby restraining the staple 100 in an installed position. Compressive forces are further created between the fifth engagement surface 124 and the first engagement surface 120, thereby aiding in the translation and rotation of the second leg 111 and the transition member 104. The rotation in the area of the second bend 132 forces the transition member 104 and the second member 103 downward and toward the first leg 110, thereby creating an offset force, whereby the second member 103 retains an attached bone at an elevation lower than the first member 102. The resultant forces 170 applied by the first leg 110 includes a horizontal component 172 that lies substantially parallel to the bridge 101 for clamping force, and a component 171 that lies substantially perpendicular to the bridge 101, thereby providing an increased retention force.

The bridge 101 having a bridge width 106 contracts when moving from the second shape 128 to the first shape 127, thereby providing additional compressive forces, and part of the translation component. The remaining portion of the translation component is created by the return of the first and fourth bends 131 and 134, to acute angles 155 and 156 as described in the first shape 127. One of ordinary skill in the art will recognize that regulating the amount of heat energy applied to the staple 100 is possible, thereby providing additional control of the amount of displacement, retention force, and the ability to utilize virtually any end use shape.

Figure 3:
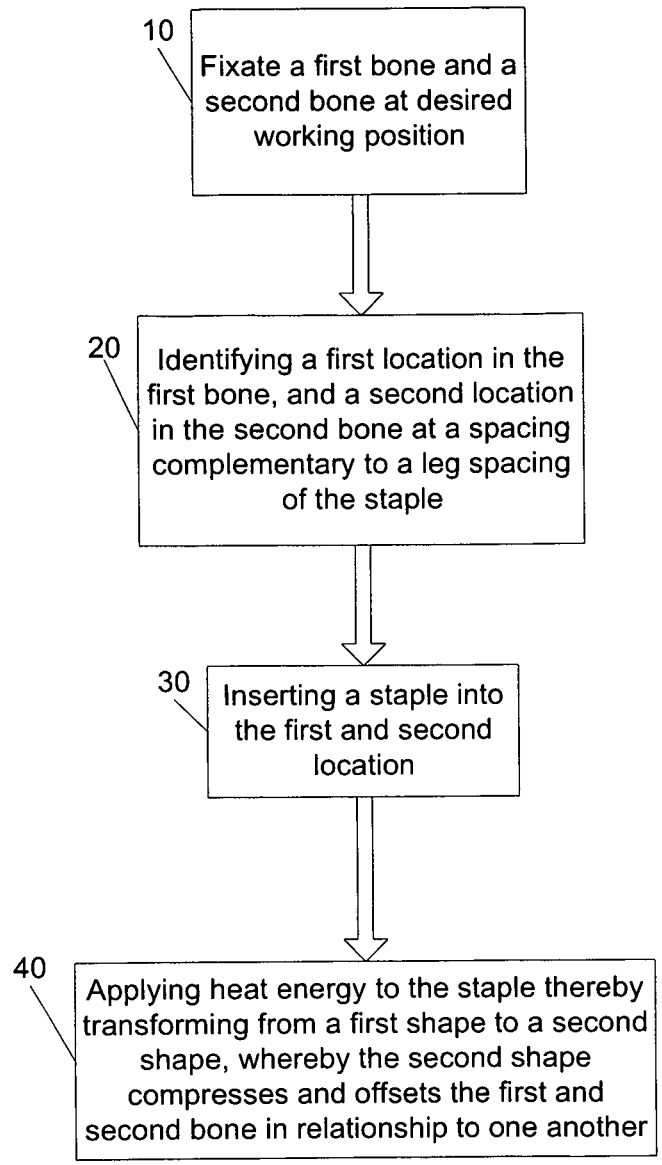
FIG. 3 provides a flowchart illustrating the method steps for utilizing the staple in an osteopathic procedure.

FIG. 3 provides a method flowchart illustrating steps for utilizing the staple 100. As shown in step 10, a user fixates a first bone 145 and a second bone 146 at a desired working position. The process continues with step 20, wherein a first location is identified in the first bone 145 and a second location is identified in the second bone at a spacing complementary to the internal clearance 126 between the first leg 110 and the second leg 111 when the staple is in the second shape 128. Step 30 provides for inserting the staple 100 into the first and second locations. By way of example, the staple 100 may be impacted into the first and second bones 145 and 146, or alternatively, a first hole 148 of a size complementary to a cross-section of the first leg 110 is drilled into the first bone 145, and a second hole 149 of a size complementary to the cross-section of the second leg 111 is drilled into the second bone 146. The spacing between the first and second holes 148 and 149 is complementary to the internal clearance 126 between the first leg 110 and the second leg 111 when the staple 100 is in the second shape 128. In the example with drilled holes, the first leg 110 is inserted into the first hole 148, and the second leg 111 is inserted into the second hole 149, thereby adapting to any offset created by anatomical conditions or creating offsets through the use of the staple 100. The process continues with step 40, wherein energy is applied to the staple 100, thereby transforming the staple 100 from the second shape 128 to the first shape 127, and compressing the first bone 145 and the second bone 146 together to promote fusion of the bones.

Figure 4:
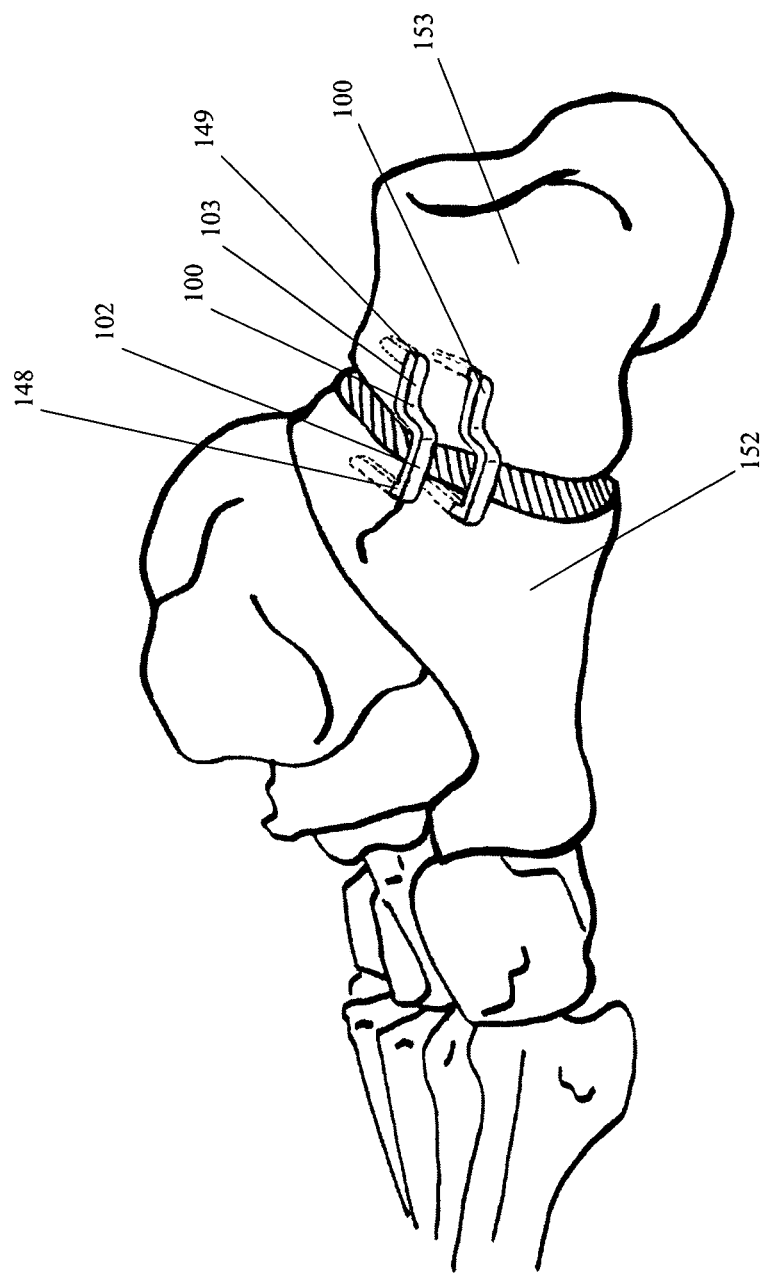
FIG. 4 provides a perspective view of an osteopathic procedure according to the first embodiment.

The staple 100 adapts to anatomical conditions that have offsets or conditions that have bones of different sizes. Illustratively, a staple 100 may be utilized to create offsets. As shown in FIG. 4, an osteotomy is performed on a foot bone 152 requiring correction, thereby producing a calcaneal fragment 153. Once the osteotomy is performed, the calcaneal fragment 153 is shifted slightly on the foot bone 152 to a position that is more advantageous for use. The bones 152 and 153 are then fixated in a position that allows a desired amount of offset complementary to the offset of the staple 100, and a first hole 148 is drilled into the foot bone 152, and a second hole 149 is drilled into the calcaneal fragment 153 at a spacing complementary to the spacing of the legs 110 and 111, of the staple 100 in the second shape 128. The staple 100 is inserted into the first and second holes 148 and 149, wherein the first member 102 is disposed adjacent to a largest bone. Upon the application of energy, the staple 100 transitions from the second shape 128 to the first shape 127 with the application of the forces previously described herein, thereby pulling the calcaneal fragment 153 toward the foot bone 152, and permanently restraining the calcaneal fragment 153 in the desired offset position. The compression of the bones 152 and 153 towards each other further promotes a bone fusion process. Upon full bone healing, the calcaneal fragment 153 reattaches to the foot bone 152.

Figure 5:
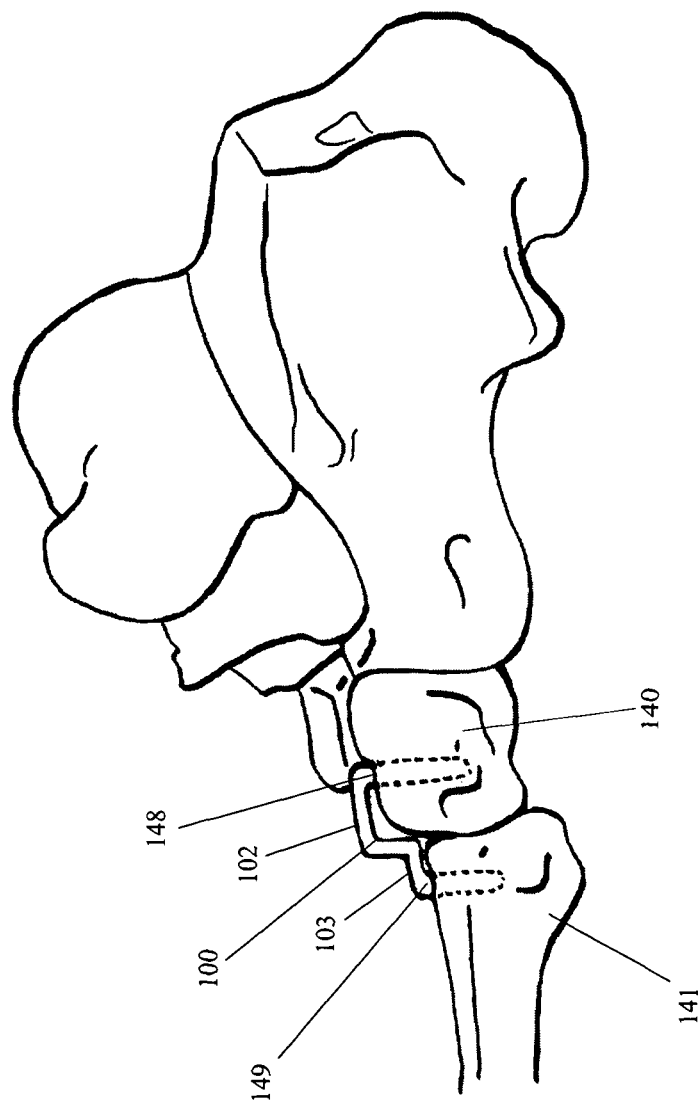
FIG. 5 provides a perspective view of a second example of an osteopathic procedure according to the first embodiment.

In a second example, the staple 100 is utilized to provide an offset to a bone joint. As shown in FIG. 5, a first foot bone 140 and a second foot bone 141 require joining. In this example, the first member 102 is utilized on the larger or first foot bone 140. The process is nearly identical to the previous procedure, wherein the bones 140 and 141 are fixated in a corrective position that provides a desired amount of offset. The offset is substantially identical to the offset between the first member 102 and the second member 104 of the staple 100. A first hole 148 is drilled into the first foot bone 140, and a second hole 149 is drilled into the second foot bone 141, at a spacing complementary to the spacing of the legs 110 and 111 of the staple 100 in the second shape 128. The staple 100 is then inserted into the drilled holes, such that the first member 102 is disposed adjacent to the first foot bone 140. Upon the application of energy, the staple 100 transitions from the second shape 128 to the first shape 127 with the application of the forces previously described herein, thereby drawing the first foot bone 140 toward the second foot bone 141, and permanently restraining the second foot bone 141 in the desired offset position. The compression between the first foot bone 140 and the second foot bone 141 forces the bones to fuse together.

While the foregoing examples have been shown to include the drilling of holes into bones, one of ordinary skill in the art will recognize that any suitable method for insertion of the staples may be used, including impaction, and the like.

While this first embodiment has been shown with one transition member 104 and two bends disposed within the bridge 101, and two legs, one of ordinary skill in the art will recognize that multiple transition members, bends, and legs may be utilized to provide increased rotation, increased offset from a first member 102 to a second member 103, or increased force application by the engagement faces.

In a second embodiment, a staple 200 is constructed from virtually any alloy exhibiting shape-memory effects, and therefore includes an original or first shape 227 (FIGS. 6A-6C) and a deformed or second shape 228 (FIGS. 7A-7C), similar to that described in the first embodiment. Likewise, it should be apparent that the staple 200 is usable at virtually any point along the transition between the second shape 228 and the first shape 227. Accordingly, an end-use shape may designate any shape between the second shape 228 and up to and including the first shape 227. The amount of heat energy applied to the deformed shape determines the extent of transition from the second shape 228 to the first shape 227.

The staple 200 includes a first leg 210, a second leg, 211, and a bridge 201, which, in the first shape 227, has a bridge width 206, and in the second shape 228, has a bridge width 207. The bridge 201 has a first end 275 and a second end 276 includes a first member 202, a second member 203, and a transition member 204. In this example, the first member 202 and the second member 203 are planar, however, one of ordinary skill in the art will recognize that the shape of members 202 and 203 may be of any form, including, arcs, angles, and the like. In this second embodiment, the first leg 210 is connected to a first end 214 of the first member 202, and a second end 215 of the first member 202 is connected to a first end 217 of the transition member 204. The second leg 211 is connected to a first end 212 of the second member 203, and a second end 213 of the second member 203 is connected to a second end 216 of the transition member 204. The staple 200 further includes a first bend 231 disposed between the first leg 210 and the first member 202, a second bend 232 disposed between the first member 202 and the transition member 204, a third bend 233 disposed between the transition member 204 and the second member 203, and a fourth bend 234 disposed between the second member 203 and the second leg 211.

The staple 200 further includes a first engagement surface 220, a second engagement surface 221, a third engagement surface 222, a fourth engagement surface 223, a fifth engagement surface 224, a sixth engagement surface 225, and a seventh engagement surface 226. The engagement surfaces 220 through 226 may extend along the complete length of the staple 200 dependent upon the cross-section of the staple 200. In this second embodiment, the first engagement surface 220 is disposed on an inner portion of the first leg 210, and the second engagement surface 221 is disposed on an inner portion of the second leg 211. The third engagement surface 222 is disposed on an inner portion of the first member 202, the fourth engagement surface 223 is disposed beneath the second member 203, and the fifth engagement surface 224 is disposed on an inner portion of the transition member 204.

The sixth engagement surface 225 is disposed on an outer portion of the first leg 210, and the seventh engagement surface 226 is disposed on an outer portion of the second leg 211. In this second embodiment, the staple 200 includes a rectangular cross-section, however, one of ordinary skill in the art will recognize that other cross-section shapes are possible, including square, round, oblong, or portions thereof.

In this second embodiment, the first engagement surface 220, the second engagement surface 221, the sixth engagement surface 225, and the seventh engagement surface 226 include barbs 219 for securing the staple 200 in position. The barbs 219 are oriented such that the legs 210 and 211 may be inserted into holes, yet may not be pulled out of the holes without damaging the engaged structure. One of ordinary skill in the art will recognize that the number and size of the barbs 219 may be adjusted to provide increased resistance forces or decreased resistance forces.

For the purpose of clarity and to provide reference points, a horizontal axis 250 and a vertical axis 251 have been provided. One of ordinary skill in the art will recognize that references to horizontal and vertical directions are complementary to the cited axes 250 and 251. It should further be understood that a vertical plane is defined as a plane passing through the vertical axis 251 and the horizontal axis 250, and a horizontal plane is perpendicular to the vertical plane. Additionally, the term "elevation" is utilized in reference to vertical displacement, wherein a lower elevation is recognized below the horizontal axis 250 and a higher elevation is recognized above the horizontal axis 250. As such, an object may move from a given elevation to a higher or lower elevation.

Figure 6A:
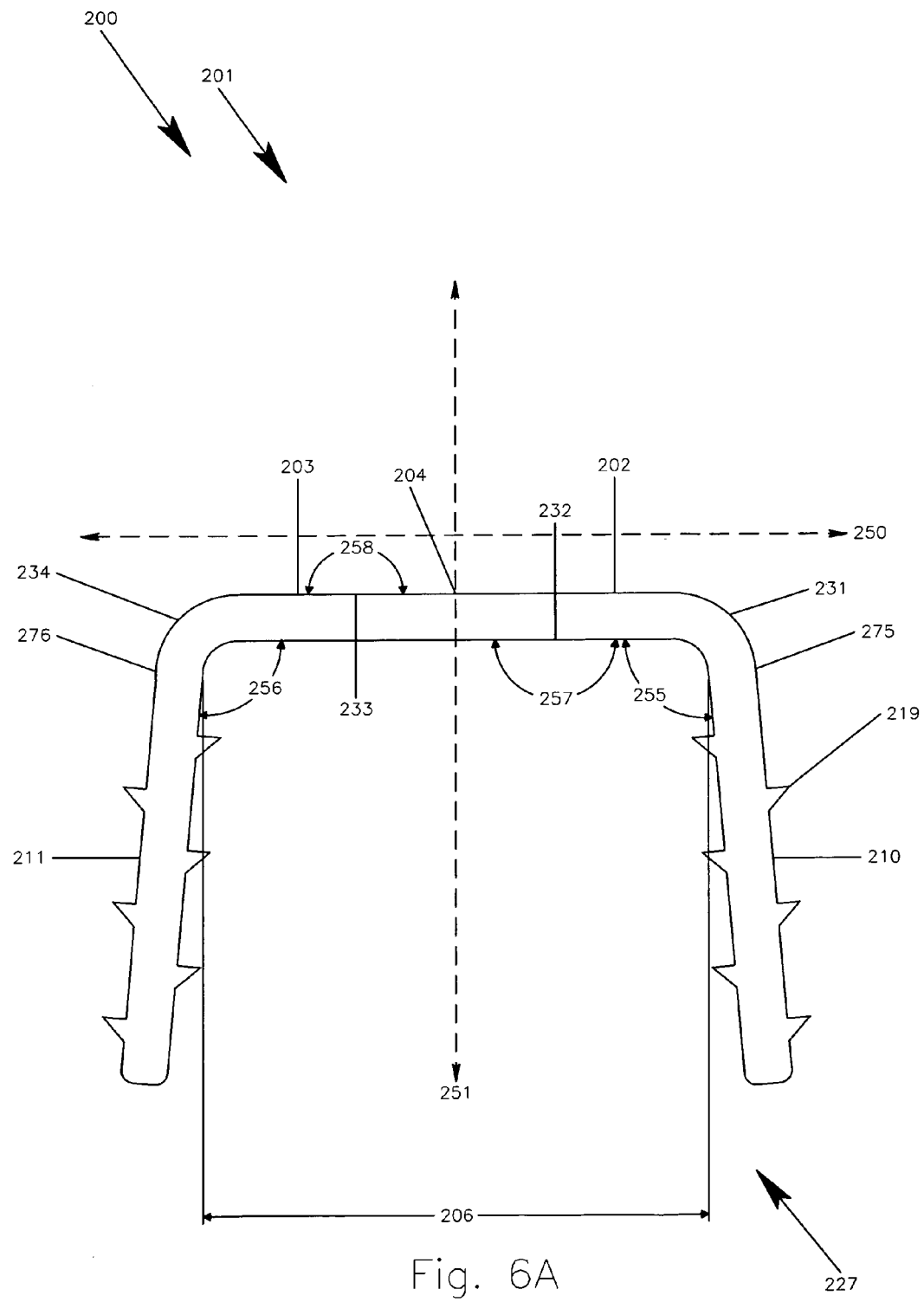
FIG. 6A provides a frontal view of a staple in a first position according to a second embodiment.
Figure 6B:
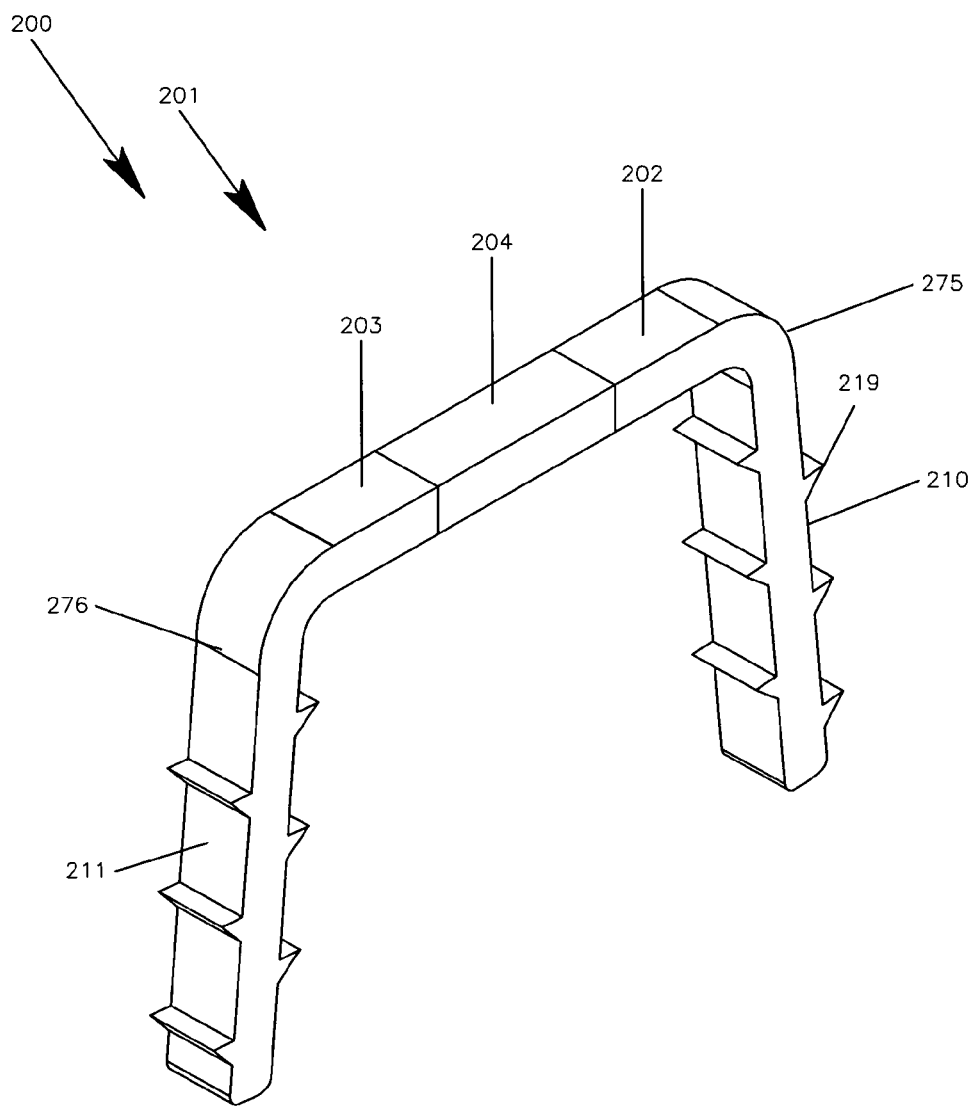
FIG. 6B provides a perspective view of the staple in the first position according to the second embodiment.
Figure 6C:
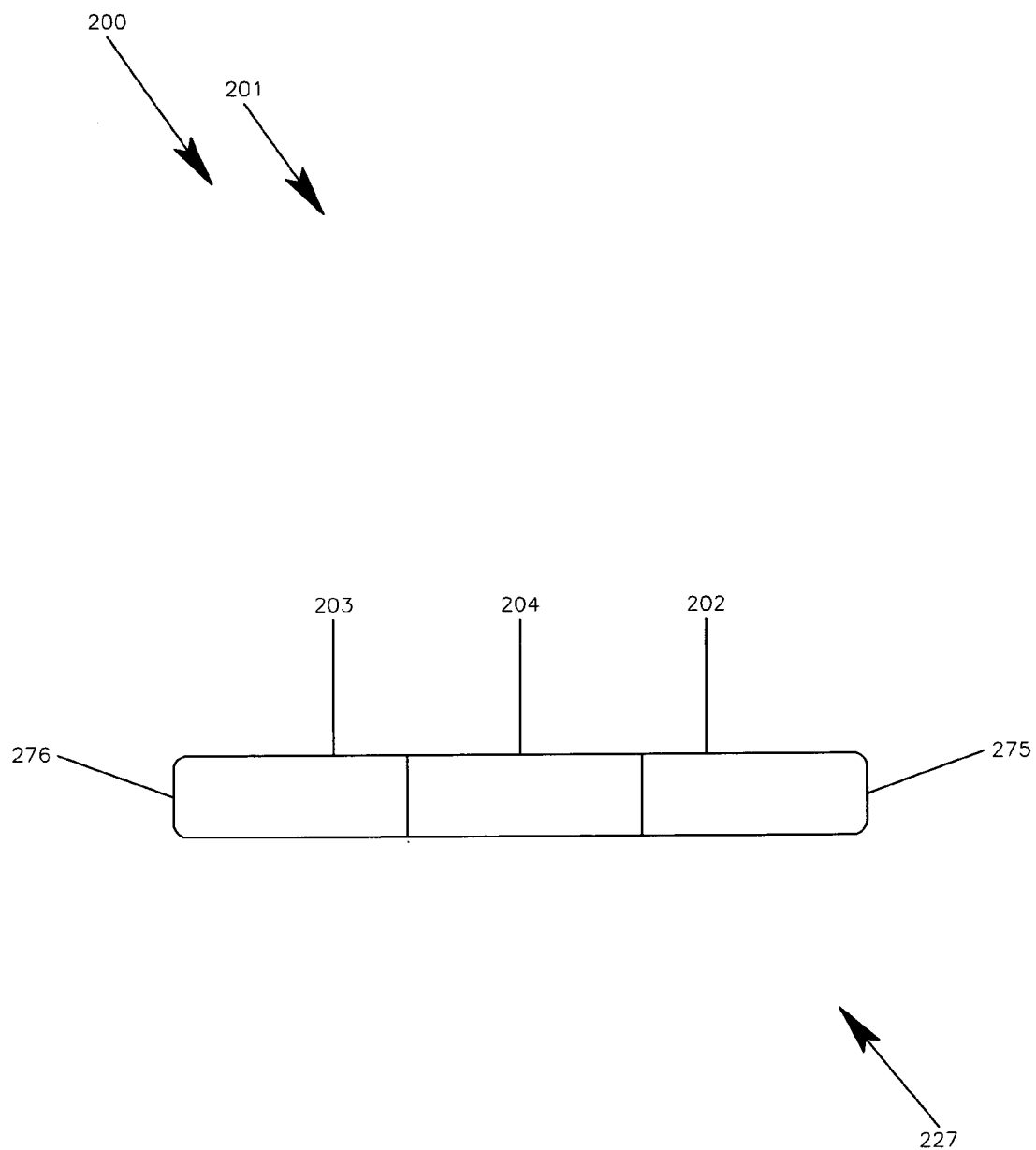
FIG. 6C provides a top view of the staple in the first position according to the second embodiment.

In the first shape 227, as shown in FIGS. 6A-6C, the first member 202 is disposed substantially parallel to the horizontal axis 250. The second member 203 and the transition member 204 are disposed substantially parallel and coplanar to the first member 202, and the first leg 210 and the second leg 211 are disposed at substantially equal angles to the respective connecting members 202 and 203. The first leg 210 is disposed at an angle 255 relative to the first member 202, and the second leg 211 is disposed at an angle 256 relative to the second member 203. Illustratively, the first and second legs 210 and 211 are disposed approximately one hundred and twenty degrees from the first and second members 202 and 203, respectively. However, one of ordinary skill in the art will recognize that other angles may be utilized, dependent upon a desired displacement. The first and second legs 210 and 211 extend from the bridge 201, such that the first leg 210 and the second leg 211 are angled away from each other, and have an internal clearance consistent with the bridge width 206. The transition member 204 is disposed at an angle 257 relative to the first member 202, and at an angle 258 relative to the second member 203. In this example of the first shape 227, the transition member 204 is disposed substantially parallel and coplanar to the planes of the first member 202 and the second member 203. It should be understood that the relationships among the first and second members 202 and 203, the first and second legs 210 and 211, and the transition member 204, as described above are exemplary only, and that these relationships may be selected dependent upon a displacement or extension force. Illustratively, the first member 202 and the second member 203 could lie in intersecting planes, the angles of the legs 210 and 211 may be different, and the transition member 204 does not have to be disposed parallel to the members. Additionally, the lengths of the first and second members 202 and 203, or the lengths of the transition member 204 may be adjusted to deliver varying results, and, accordingly, all such adjustments should be construed as part of this disclosure.

Figure 7A:
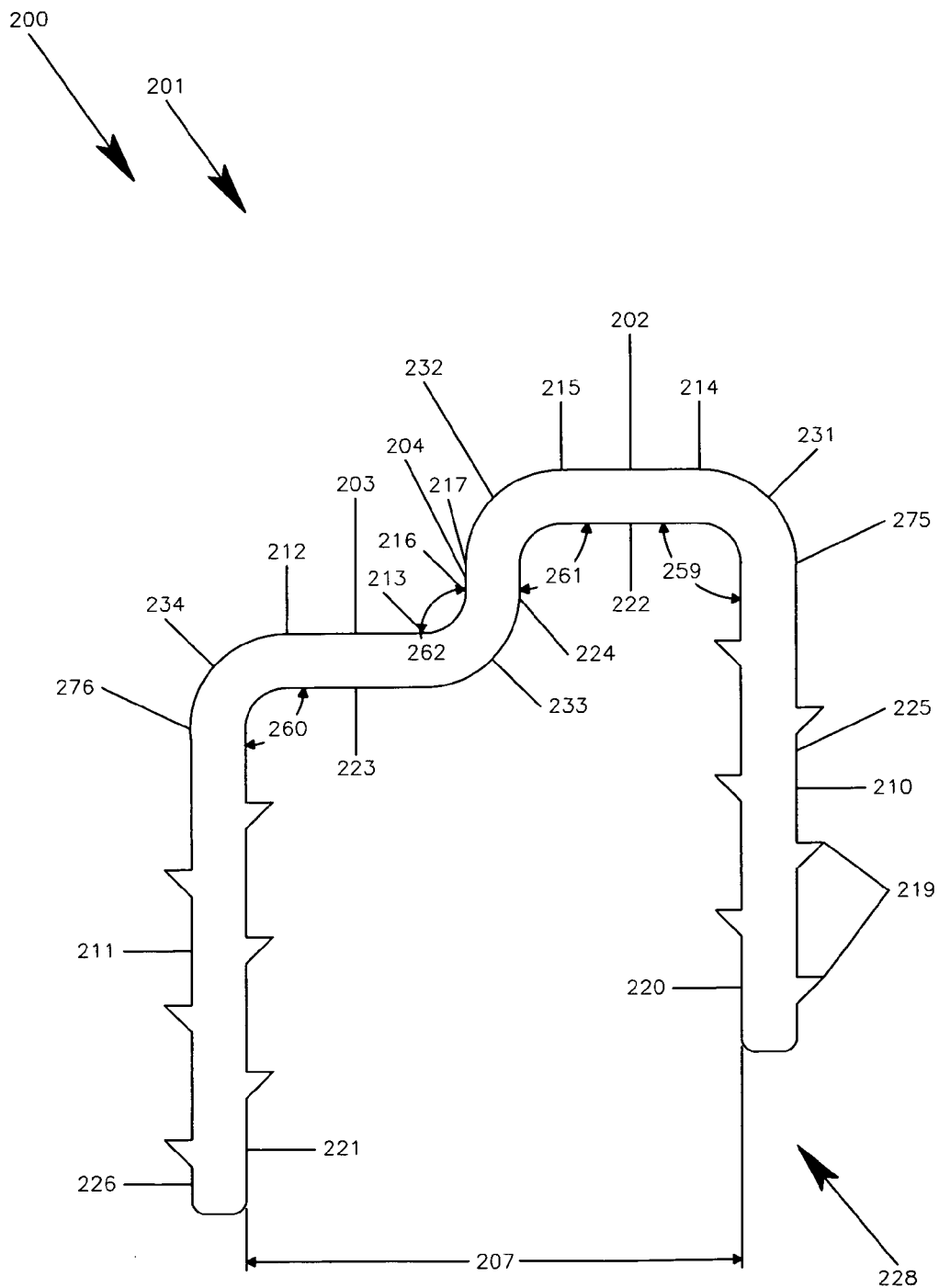
FIG. 7A provides a frontal view of a staple in a second position according to the second embodiment.
Figure 7B:
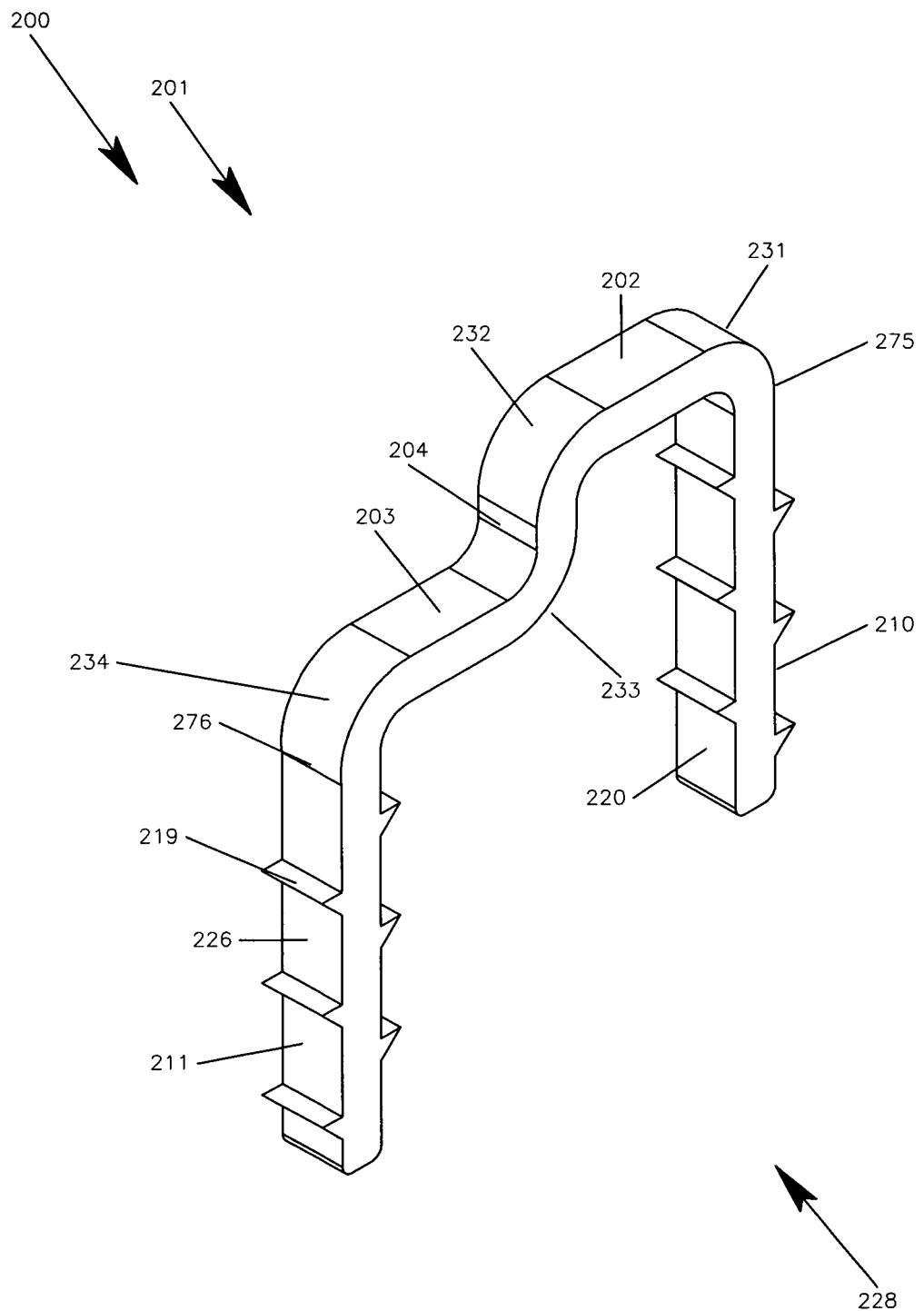
FIG. 7B provides a perspective view of the staple in the second position according to the second embodiment.
Figure 7C:
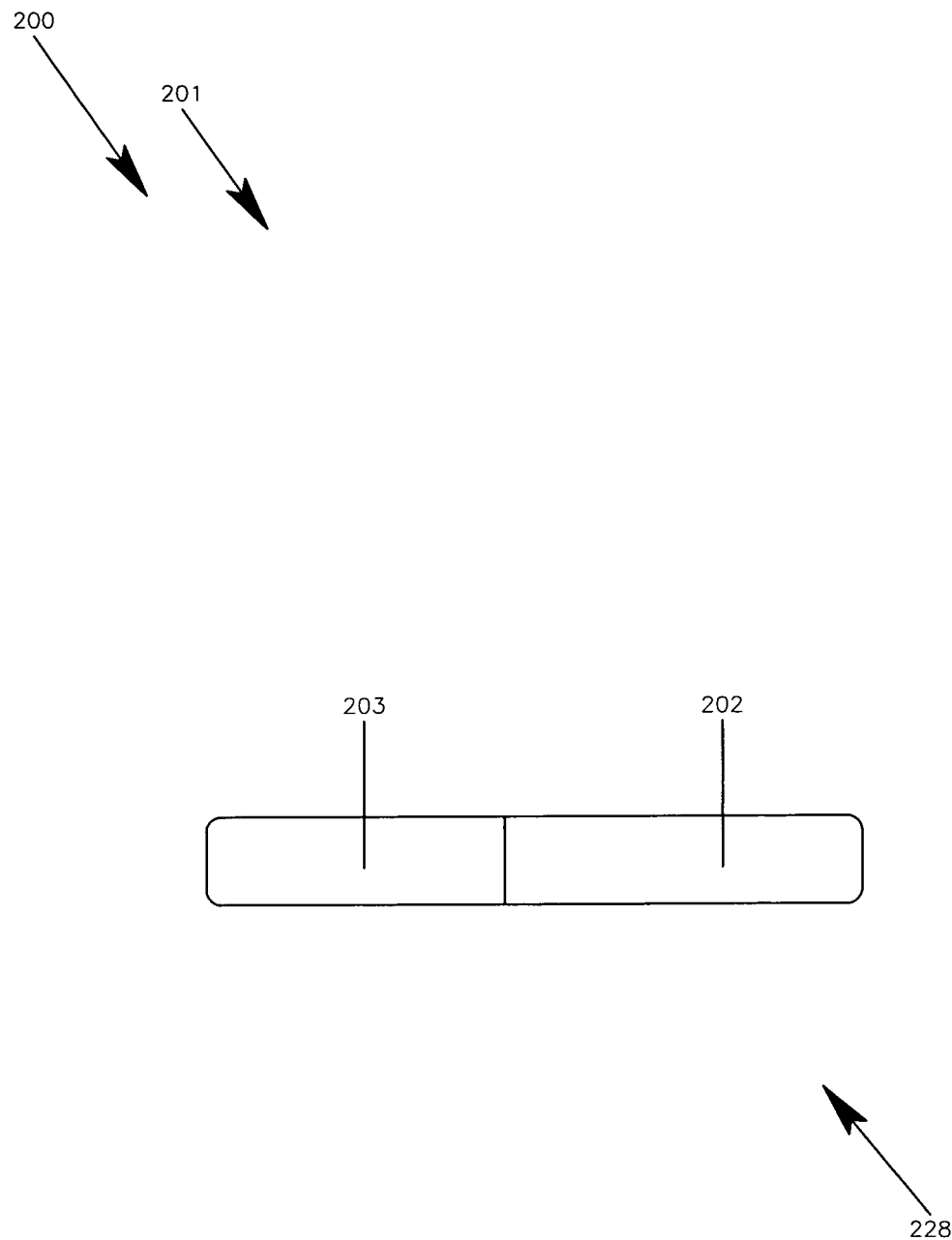
FIG. 7C provides a top view of the staple in the second position according to the second embodiment.

In the second shape 228, the staple 200 is deformed as shown in FIGS. 7A-7C, such that the first member 202 and the second member 203 are offset and substantially parallel to each other, and the first leg 210 and the second leg 211 are substantially perpendicular to the first member 202 and the second member 203. As such, the first bend 231 is contracted to an angle 259, and the fourth bend 234 is contracted to an angle 260. Illustratively, the angles 259 and 260 span approximately ninety degrees. Similarly, the second bend 232 contracts to angle 261, and the third bend 233 contracts to angle 262, such that the transition member 204 is disposed substantially perpendicular to the first member 202 and the second member 203, thereby decreasing the clearance between the legs 210 and 211 to an internal clearance equivalent to the bridge width 207. Illustratively, the transition member 204 is disposed at an angle of approximately ninety degrees relative to the first and second members 202 and 203. While the staple 200 has been shown with the legs 210 and 211 substantially perpendicular to the first and second members 202 and 203, and the transition member 204 disposed at an angle of approximately ninety degrees relative to the first and second members 202 and 203, one of ordinary skill in the art will recognize that other angles besides those shown may be utilized to deliver varying forces and lateral displacements. It should further be recognized that the use of parallel legs is conducive to insertion of a staple into pre-drilled holes; however, other angles may be utilized to address alternative situations, including the insertion of one leg at a time.

Upon the application of heat energy, the staple 200 in a deformed or second shape 228 (deformed martensitic phase), commences to change from the martensitic state to the austenitic state. Upon completion of the austenitic phase change, the staple 200 has returned to the original or first shape 227. Upon cooling, the staple 200 retains the original or first shape 227. One of ordinary skill in the art will recognize that upon the transformation of a shape memory alloy to the original shape 227, a force is created, and accordingly, the staple 200 may be utilized in applications where retaining and residual forces are required.

Figure 6D:
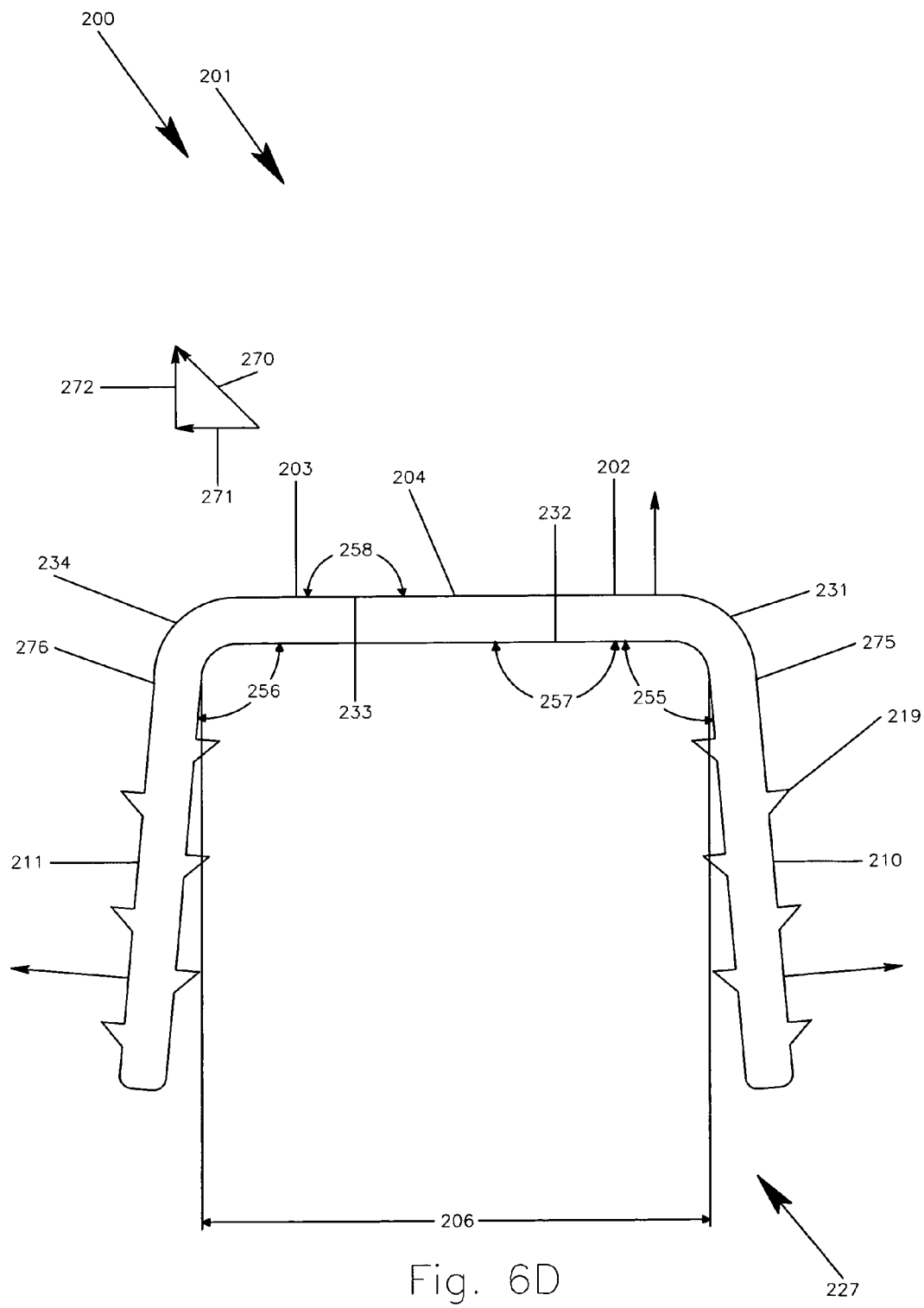
FIG. 6D provides a frontal view of the staple in the first position including forces generated by the staple according to the second embodiment.

In this second embodiment, the phase change from the deformed or second shape 228 to the original or first shape 227 creates forces as shown in FIG. 6D. The first bend 231 moves in an arc from the angle 259 (approximately ninety degrees) to a second more obtuse angle 255 (approximately one hundred degrees), thereby rotating the first leg 210 a prescribed distance away from the second leg 211. In a similar fashion, the fourth bend 234 moves from the angle 260 that is substantially perpendicular relative to the second member 203 to the angle 256 that is a more obtuse angle, thereby rotating the second leg 211 away from the first leg 210 a prescribed distance.

Additionally, the second bend 232 moves from the angle 261 (substantially ninety degrees) to angle 257 (approximately one hundred and eighty degrees), and the third bend 233 moves from the angle 262 (perpendicular angle position associated with the second shape 228) to the angle 258 (approximately one hundred and eighty degrees associated with the first shape 227). Accordingly, in the first shape 227 the transition member 204 is in a position that is substantially parallel and coplanar relative to the first member 202 and the second member 203. The rotation of the transition member 204 to the substantially parallel and coplanar position of the first shape 227 pushes the fourth bend 234, and the second leg 211 away from the first leg 210, such that the bridge width 206 of the first shape 227 is greater than the bridge width 207 of the second shape 228, thereby providing a translation component across the bridge 201 and increased extension forces at the legs 210 and 211.

In this second embodiment, extension forces are created between the sixth and seventh engagement surfaces 225 and 226, thereby providing distraction between connected bones so as to decompress nerves that may be trapped between bone segments. The rotation in the area of the second bend 232 forces the transition member 204 and the second member 203 upward, thereby creating an offset force, whereby the second member 203 moves an attached bone at an elevation lower than the first member 202 to the plane even with the first member 202. Extension forces are further created in the horizontal direction by the first member 202 and the second member 203 as the transition member 204 and the second member 203 move into the same plane. The resultant forces 270 applied by the second leg 211 and the second member 203 include a horizontal component 271 that lies substantially parallel to the bridge 201 for extending force, and a component 272 that lies substantially perpendicular to the bridge 201, thereby providing an offsetting capability to realign bone segments that have slipped relative to one another.

The bridge 201 having a bridge width 207 extends when moving from the second shape 228 to the first shape 227, thereby providing part of the translation component. The remaining portion of the translation component is created by the extension of the first and fourth bends 231 and 234, to obtuse angles 255 and 256 as described in the first shape 227. One of ordinary skill in the art will recognize that regulating the amount of energy applied to the staple 200 is possible, thereby providing additional control of the amount of displacement, retention force, and the ability to utilize virtually any end use shape along the transition from the second shape 228 to the first shape 227.

Figure 8A:
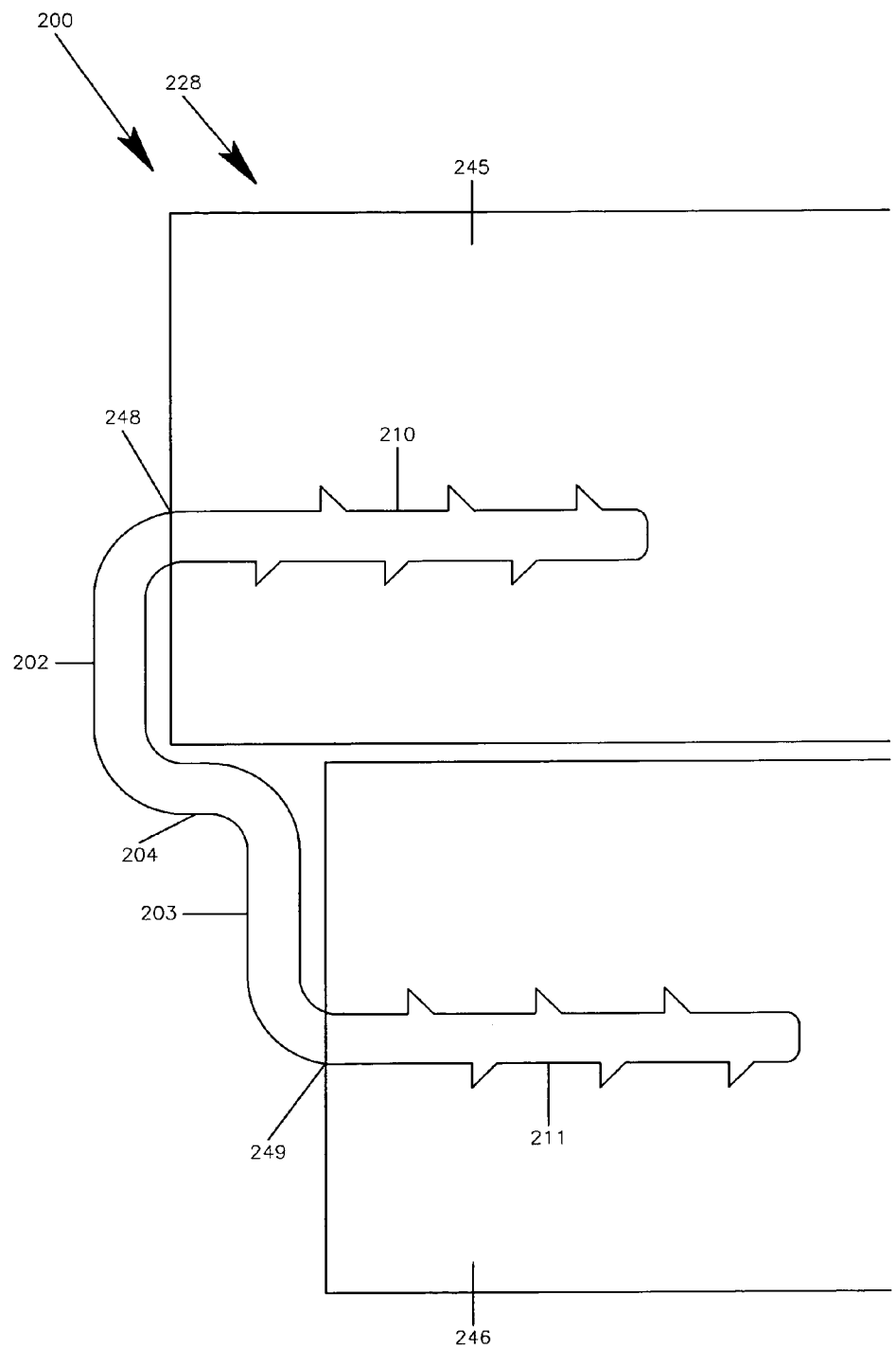
FIG. 8A provides a section view of the staple secured to misaligned bones according to the second embodiment.

The staple 200 adapts to existing distracted bones such as those shown in FIG. 8A. The ability to adapt to distracted bones, particularly vertebrae in a spondylosis, allows forcible distraction and restraint of the bones 245 and 246 in the distracted position. Upon the transformation to the first shape 227, the first bone 245 and the second bone 246 are straightened such that contact between the bones 245 and 246 is not possible, thereby allowing a nerve cord to be decompressed.

Further advantages of the staple 200 include the ability to move a first bone 245 and a second bone 246 into an anatomically correct position by applying heat energy to the staple 200 until the bone 246 attached to the second leg 211 is aligned with the bone 245 attached to the first leg 210. Accordingly, virtually any amount of correction and restraint may be applied.

Figure 8B:
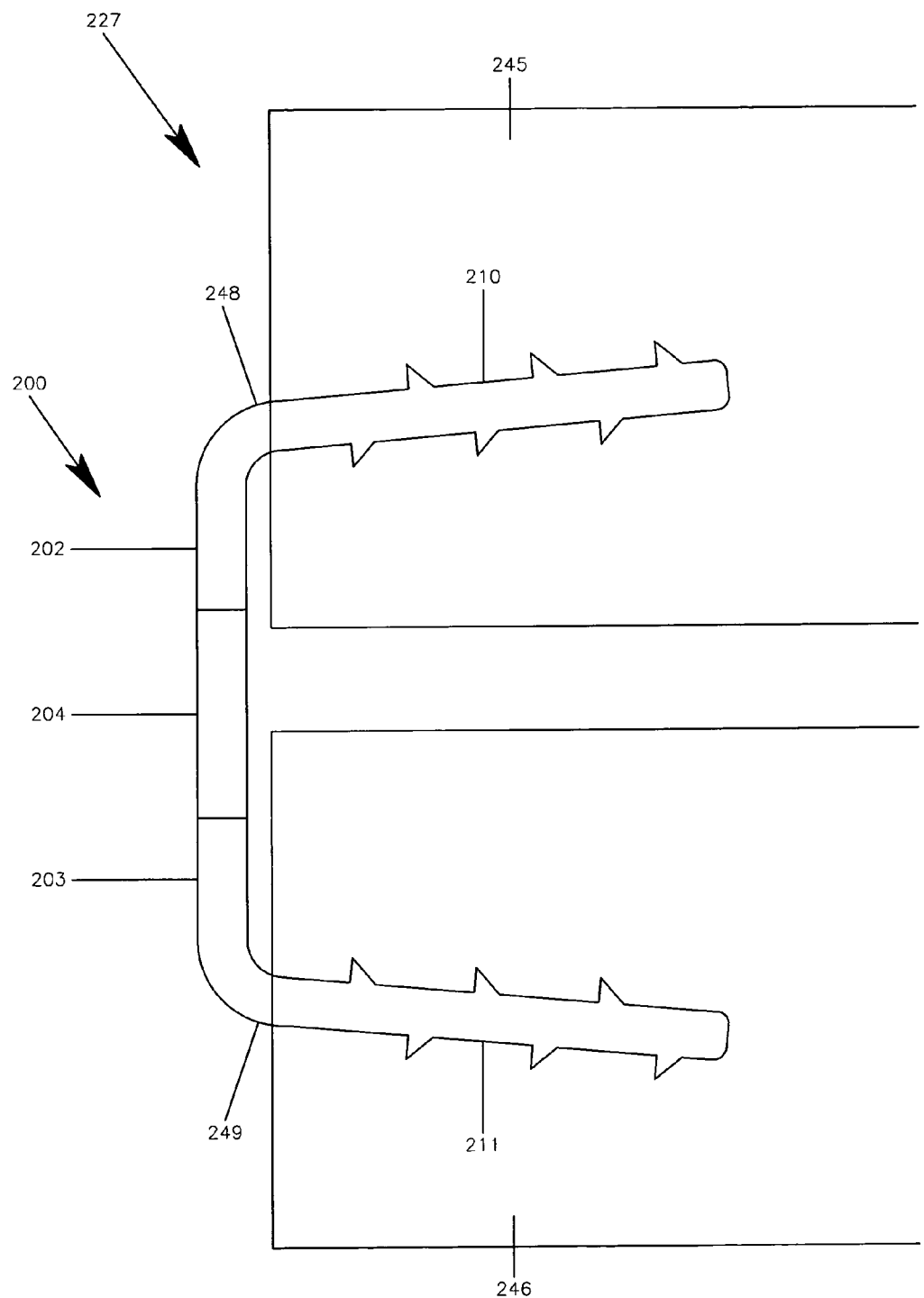
FIG. 8B provides a section view of the bones and staple after spondylosis according to the second embodiment.
Figure 8C:
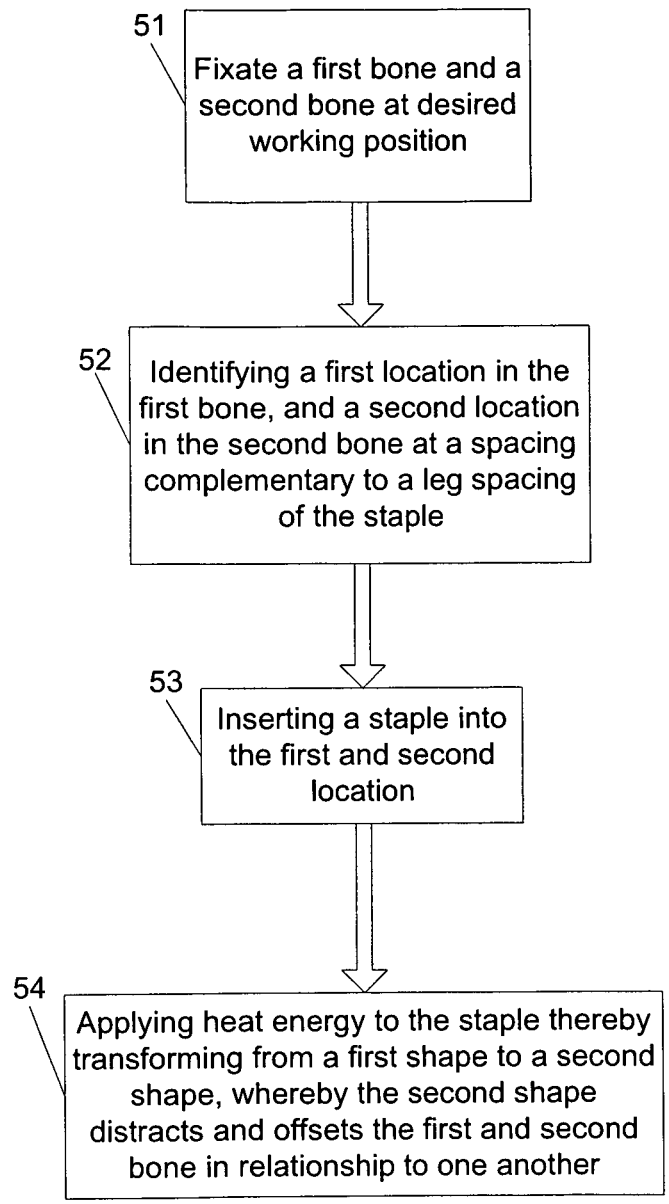
FIG. 8C provides a flowchart illustrating the method steps for utilizing the staple in spondylosis according to the second embodiment.

FIG. 8C provides a method flowchart illustrating steps for utilizing the staple 200. As shown in step 51, a user fixates a first bone 245 and a second bone 246 at a desired working position. The process continues with step 52, wherein a first location is identified in the first bone 245 and a second location is identified in the second bone 246 at a spacing complementary to the internal clearance between the first leg 210 and the second leg 211 when the staple is in the second shape 228. Step 53 provides for inserting the staple 200 into the first and second locations. By way of example, the staple 100 may be impacted into the first and second bones 245 and 246, or alternatively, a first hole 248 of a size complementary to a cross-section of the first leg 210 is drilled into the first bone 245, and a second hole 249 of a size complementary to the cross-section of the second leg 211 is drilled into the second bone 246. The spacing between the first and second holes 248 and 249 is complementary to the internal clearance between the first leg 210 and the second leg 211 when the staple 200 is in the second shape 228. In the example with drilled holes, the first leg 210 is inserted into the first hole 248, and the second leg 211 is inserted into the second hole 249, thereby adapting to any offset created by anatomical conditions or existing bone distractions. The process continues with step 54, wherein heat energy is applied to the staple 200, thereby transforming the staple 200 from the second shape 228 to the first shape 227, and distracting the first bone 245 and the second bone 246, as shown in FIG. 8B.

While the foregoing example has been shown to include drilled holes as securing points for the staple 200, one of ordinary skill in the art will recognize that any suitable method for insertion of the staples may be used, including impaction, and the like.

One of ordinary skill in the art will recognize that the transition member 204 of the staple may be lengthened or shortened to accommodate virtually any amount of distraction, and, as disclosed in the first embodiment, the angle of the transition member 204 may be adjusted to achieve a desired result. Further, it should be further understood that this invention is not restricted to the motion of a second member up to a level of the first member, as one of ordinary skill in the art will recognize that a second member 203 may move to any elevation above a current elevation.

While this second embodiment has been shown with barbs 219 disposed along the legs 210 and 211, it should be understood that this invention is compatible with other methods for securing the staple 200 to bones, including legs that move from a first shape to a second shape.

It should further be understood in this second embodiment has been shown with one transition member 204 and two bends disposed within the bridge 201, one of ordinary skill in the art will recognize that multiple transition members and bends may be utilized to provide increased rotation, increased offset from a first member 202 to a second member 203, or increased force application by the engagement faces.

Although the present invention has been described in terms of the foregoing preferred embodiment, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

I claim:

1. A staple, comprising:
(a) a bridge, comprising:
   (i) a transition member comprised of shape memory material,
   (ii) a first member comprised of shape memory material, the first member coupled to the transition member, and
   (iii) a second member comprised of shape memory material, the second member coupled to the transition member, wherein,
      (A) the first member is in a first plane,
      (B) the second member is in a second plane,
      (C) the first plane and the second plane are substantially parallel to each other, and
      (D) the second plane is at an elevation different than the first plane;
(b) a first leg comprised of shape memory material, wherein the first leg is coupled to the first member;
(c) a second leg comprised of shape memory material, wherein the second leg is coupled to the second member, wherein (i) the first leg is substantially parallel to the second leg, and
(ii) the staple is configured such that when energy is applied to the staple the staple moves from a first shape to a second shape wherein
 (A) the first leg and second leg are not parallel to one another, and
 (B) the difference of the elevation between the first plane and the second plane has changed.

2. The staple according to claim 1, further comprising:
a first plurality of legs comprised of shape memory material, wherein the legs are coupled to the first member; and
a second plurality of legs comprised of shape memory material, wherein the second plurality of legs are coupled to the second member.

3. A method of offsetting a first bone relative to an adjacent second bone, comprising:
(a) providing a staple configured to deform from a first shape to a second shape, wherein the staple comprises
 (i) a bridge, comprising:
  (A) a transition member comprised of shape memory material,
  (B) a first member comprised of shape memory material, the first member coupled to the transition member, and
  (C) a second member comprised of shape memory material, the second member coupled to the transition member, wherein,
   (I) the first member is in a first plane,
   (II) the second member is in a second plane,
   (III) the first plane and the second plane are substantially parallel to each other, and
   (IV) the second plane is at an elevation different than the first plane;
 (ii) a first leg comprised of shape memory material, wherein the first leg is coupled to the first member;
 (iii) a second leg comprised of shape memory material, wherein the second leg is coupled to the second member, wherein
  (A) the first leg is substantially parallel to the second leg, and
  (B) the staple is configured such that when energy is applied to the staple the staple moves from a first shape to a second shape wherein
   (I) the first leg and second leg are not parallel to one another. and
   (II) the difference of the elevation between the first plane and the second plane has changed;
(b) fixating the first bone and the second bone in a desired working position;
(c) inserting the first leg into the first bone and the second leg into the second bone; and
(d) applying energy to the staple, thereby moving the staple from the first shape to the second shape, wherein the moving from the first shape to the second shape forces and restrains the second bone in an offset position.

4. The method claim 3, wherein
(a) the length of the bridge in the second shape is shorter than the length of the bridge in the first shape,
(b) the first leg and the second leg are angled toward each other in the second shape, and
(c) the transition member of the second shape is more perpendicular to the first plane and second plane than the transition member of the first shape.

5. The staple according to claim 1, wherein
(a) the length of the bridge in the second shape is shorter than the length of the bridge in the first shape,
(b) the first leg and the second leg are angled toward each other in the second shape, and
(c) the transition member of the second shape is more perpendicular to the first plane and second plane than the transition member of the first shape.

* * * * *